US008206704B2

(12) United States Patent
Waldman et al.

(10) Patent No.: US 8,206,704 B2
(45) Date of Patent: Jun. 26, 2012

(54) USE OF GCC LIGANDS

(75) Inventors: Scott A. Waldman, Ardmore, PA (US); Giovanni Mario Pitari, Philadelphia, PA (US); Jason Park, Philadelphia, PA (US); Stephanie Schulz, West Chester, PA (US); Henry R. Wolfe, Glenmoore, PA (US); Wilhelm Lubbe, Philadelphia, PA (US)

(73) Assignee: Thomas Jefferson University, Philadelphia, PA (US)

( * ) Notice: Subject to any disclaimer, the term of this patent is extended or adjusted under 35 U.S.C. 154(b) by 912 days.

(21) Appl. No.: 10/775,481

(22) Filed: Feb. 10, 2004

(65) Prior Publication Data

US 2004/0258687 A1 Dec. 23, 2004

Related U.S. Application Data

(60) Provisional application No. 60/446,730, filed on Feb. 10, 2003.

(51) Int. Cl.
*A61K 38/00* (2006.01)
*A61K 39/395* (2006.01)
*A61K 39/00* (2006.01)
*A61P 43/00* (2006.01)
*A61P 35/00* (2006.01)
*A61P 35/04* (2006.01)

(52) U.S. Cl. ............... 424/130.1; 424/138.1; 424/142.1; 424/143.1; 424/178.1; 424/181.1; 514/1.1; 514/18.9; 514/19.2; 514/19.8

(58) Field of Classification Search .................. None
See application file for complete search history.

(56) References Cited

U.S. PATENT DOCUMENTS

| 4,601,896 | A | 7/1986 | Nugent et al. |
| 4,729,893 | A | 3/1988 | Letcher et al. |
| 4,849,227 | A | 7/1989 | Cho et al. |
| 4,963,263 | A | 10/1990 | Kauvar et al. |
| 5,133,866 | A | 7/1992 | Kauvar et al. |
| 5,143,854 | A | 9/1992 | Pirrung et al. |
| 5,217,869 | A | 6/1993 | Kauvar et al. |
| 5,221,736 | A | 6/1993 | Coolidge et al. |
| 5,223,409 | A | 6/1993 | Ladner et al. |
| 5,225,539 | A | 7/1993 | Winter et al. |
| 5,252,743 | A | 10/1993 | Barrett et al. |
| 5,270,170 | A | 12/1993 | Schatz et al. |
| 5,271,961 | A | 12/1993 | Mathiowitz et al. |
| 5,288,514 | A | 2/1994 | Ellman et al. |
| 5,324,483 | A | 6/1994 | Cody et al. |
| 5,338,665 | A | 8/1994 | Schatz et al. |
| 5,340,474 | A | 8/1994 | Kauvar |
| 5,350,741 | A | 9/1994 | Takada et al. |
| 5,366,862 | A | 11/1994 | Venton et al. |
| 5,384,261 | A | 1/1995 | Winkler et al. |
| 5,395,750 | A | 3/1995 | Dillon et al. |
| 5,399,347 | A | 3/1995 | Trentham et al. |
| 5,405,783 | A | 4/1995 | Pirrung et al. |
| 5,412,087 | A | 5/1995 | McGall et al. |
| 5,420,328 | A | 5/1995 | Campbell et al. |
| 5,424,186 | A | 6/1995 | Fodor et al. |
| 5,518,888 | A | 5/1996 | Waldman et al. |
| 5,530,101 | A | 6/1996 | Queen et al. |
| 5,585,089 | A | 12/1996 | Queen et al. |
| 5,601,990 | A | 2/1997 | Waldman et al. |
| 5,731,159 | A | 3/1998 | Waldman et al. |
| 5,879,656 | A * | 3/1999 | Waldman ..................... 424/1.49 |
| 5,928,873 | A | 7/1999 | Waldman et al. |
| 5,962,220 | A | 10/1999 | Waldman et al. |
| 6,060,037 | A * | 5/2000 | Waldman ..................... 424/1.65 |
| 6,087,109 | A * | 7/2000 | Waldman ......................... 435/6 |
| 6,251,439 | B1 * | 6/2001 | Baron .......................... 424/678 |
| 6,268,159 | B1 | 7/2001 | Waldman et al. |
| 6,767,704 | B2 * | 7/2004 | Waldman et al. ................. 435/6 |
| 7,041,786 | B2 | 5/2006 | Shailubhai |
| 7,744,870 | B1 * | 6/2010 | Waldman .................. 424/130.1 |
| 7,854,933 | B2 * | 12/2010 | Waldman et al. .......... 424/181.1 |
| 2001/0029019 | A1 | 10/2001 | Waldman et al. |
| 2004/0180002 | A1 * | 9/2004 | Young et al. ................ 424/1.49 |
| 2004/0197328 | A1 * | 10/2004 | Young et al. ............... 424/141.1 |
| 2004/0258693 | A1 * | 12/2004 | Young et al. ............... 424/155.1 |
| 2006/0019256 | A1 * | 1/2006 | Clarke et al. ....................... 435/6 |

FOREIGN PATENT DOCUMENTS

| WO | WO9511694 | 5/1995 |
| WO | WO9742220 | 11/1997 |
| WO | WO9742506 | 11/1997 |
| WO | WO01/25266 | 4/2001 |
| WO | 01/73133 | 10/2001 |
| WO | 02/22885 | 3/2002 |
| WO | 02/070018 | 9/2002 |

OTHER PUBLICATIONS

Freshney (Culture of Animal Cells, A Manual of Basic Technique, Alan R. Liss, Inc., 1983, New York, p. 4).* Dermer (Bio/Technology, 1994, 12:320).*
Drexler et al (Leukemia and Lymphoma, 1993, 9:1-25).*
Zellner et al. (Clin. Can. Res., 1998, 4:1797-1802).*
Gura (Science, 1997, 278:1041-1042).*
Kaiser (Science, 2006, 313, 1370).*
Jain (Sci. Am., 1994, 271:58-65).*
Curti (Crit. Rev. in Oncology/Hematology, 1993, 14:29-39).*
Roitt et al., (Immunology, Third Edition (Mosby, London England) p. 1.7).*
Harlow and Lane (Antibodies, a Laboratory Manual, Cold Spring Harbor Laboratory Press, 1988, p. 141-142).*
Queen et al. (Proc. Natl. Acad. Sci. 1989, vol. 86, pp. 10029-10033).*
Riechmann et al (Nature vol. 332:323-327 1988).*
Cohen (Int J Radiat Oncol Biol Phys, 1987, 13:251-8).*
Wolfe et al. (The J. of Nuclear Medicine Mar. 2002, 43: 392-399).*

(Continued)

*Primary Examiner* — Peter J Reddig
(74) *Attorney, Agent, or Firm* — Pepper Hamilton LLP

(57) ABSTRACT

Proliferation of colorectal, gastric and esophageal cancer cells is inhibited by administering ST receptor ligand. The number of ST receptor molecules on the surface of a colorectal cell or metastasized colorectal cancer cell are increased by administering an ST receptor ligand such that ligand comes into contact with an ST receptor on the surface of the colorectal cell. Pharmaceutical compositions comprise sterile, pyrogen free ST receptor ligand and a pharmaceutically acceptable carrier or diluent. Metastasized colorectal cancer is treated or imaged by increasing the number of ST receptor molecules on the surface of a metastasized colorectal cancer cell and then administering a pharmaceutical composition containing components that target the ST receptor for delivery of a therapeutic agent or imaging agent. Methods of detecting metastasized colorectal cancer are disclosed. Methods of delivering active compounds to a colorectal cell in an individual are disclosed.

26 Claims, 4 Drawing Sheets

OTHER PUBLICATIONS

Dorland's Medical Dictionary for Healthcare Consumers (salt-losing crisis/salt-losing syndrome, Elsevier, http://www.mercksource.com/pp/us/cns/cns_home.jsp, 2007).*

Taber's Cyclopedic Medical Dictionary (1985, F.A. Davis Company, Philadelphia, p. 274).*

Busken, C et al. (Digestive Disease Week Abstracts and Itinerary Planner, 2003, abstract No. 850).*

Kaiser (Science, 2006, 313: 1370).*

Krontiris and Capizzi (Internal Medicine, 4th Edition, Editor-in-chief Jay Stein, Elsevier Science, 1994 Chapters 71-72, pp. 699-729).*

Carter, S. K. et al. (Chemotherapy of Cancer; Second edition; John Wiley & Sons : New York, 1981; appendix C).*

Carrithers et al. (Kidney Int. 2004 65: 40-53).*

Ames, J. B. et al., "Three-dimensional structure of guanylyl cyclase activating protein-2, a calcium-sensitive modulator of photoreceptor guanylyl cyclases," *J. Biol. Chem.*, (1999), 274, 19329-19337.

Andric et al. "Dependence of soluble guanylyl cyclase activity on calcium signaling in pituitary cells," *J. Biol. Chem.* (2001), 276, 844-849.

Berridge, M. J. et al., "Calcium—a life and death signal," *Nature* (1998), 395, 645-648.

Bhattacharya, J. et al., "Rise of intracellular free calcium levels with activation of inositol triphosphate in a human colonic carcinoma cell line (COLO 205) by heat-stable enterotoxin of *Escherichia coli*," *Biochim. Biophys. Acta* (1998), 1403, 14.

Biel et al., "Cyclic nucleotide-gated channels—mediators of NO:cGMP-regulated processes," *Naunyn Schmiedeberg's Arch. Pharmacol.* (1998), 358, 140-144.

Birkenkamp-Demtroder, K. et al., "Gene expression in colorectal cancer," *Cancer Res.* (2002), 62, 4352-4363.

Blanchard R.K. et al., "Upregulation of rat intestinal uroguanylin mRNA by dietary zinc restriction," *Am. J. Physiol.* (1997) 272 (5Pt 1) G972-978.

Brenner et al., "Encoded combinatorial chemistry," *Proc. Natl. Acad. Sci* . USA (Jun. 1992), 89:5381-5383.

Briskey, E. N. et al., "Colorectal cancer: update on recent advances and their impact on screening protocols," *J. Natl. Med. Assoc.* (2000), 92(5), 222-230.

Buset, M. et al., "Inhibition of human colonic epithelial cell proliferation in vivo and in vitro by calcium," *Cancer Res.* (1986), 46, 5426-5430.

Butt, E., "(Rp)-8-pCPT-cGMPS, a novel cGMP-dependent protein kinase inhibitor," *Eur. J. Pharmacol.* (1994), 269(2), 265-268.

Carrithers et al., "Guanylyl cyclase C is a selective marker for metastatic colorectal tumors in human extraintestinal tissues," *Proc Natl Acad Sci USA* (1996) 93(25):14827-32.

Chan et al., "Amino acid sequence of heat-stable enterotoxin produced by *Escherichia coli* pathogenic for man," *J. Biol. Chem.* (1981), 256(15):7744-6.

Chao, A. C. et al., "Activation of intestinal CFTR Cl—channel by heat-stable enterotoxin and guanylin via cAMP-dependent protein kinase," EMBO J. (1994) 1;13(5):1065-72.

Cohen et al., "Guanylin mRNA expression in human intestine and colorectal adenocarcinoma," *Lab. Invest.* (1998), 78(1), 101-108.

Cull M.G. et al., "Screening for receptor ligands using large libraries of peptides linked to the C terminus of the lac repressor," *Proc. Natl. Acad. Sci. USA* (Mar. 1992), 89:1865-1869.

Currie, M.G. et al., "Guanylin: an endogenous activator of intestinal guanylate cyclase," *Proc. natl. Acad. Sci. USA* (1992) 89:947-951.

Devor, D. C. et al., "Modulation of K+ channels by arachidonic acid in T84 cells. I. Inhibition of the Ca(2+)-dependent K+ channel," *Am. J. Physiol.* (1998), 274, C138-C148.

Dostmann, W. R. et al., "(RP)-cAMPS inhibits the cAMP-dependent protein kinase by blocking the cAMP-induced conformational transition," *FEBS Lett.* (1995), 375(3), 231-234.

Dayhoff, M.O. et al., "A model of evolutionary change in proteins" in *Atlas of Protein Sequence and Structure*, Nat. Biomed. Res. Foundation, Washington D.C. (1978), vol. 5, supp. 3, chapter 22, 345-352.

Dzeja, C. et al., "Ca2+ permeation in cyclic nucleotide-gated channels," *Embo J.* Jan. 4, 1999;18(1):131-44. 18, 131144.

Fodor, S. P. A. et al., "Light-directed, spatially addressable parallel chemical synthesis," *Science* vol. 251, Issue 4995, 767-773 (Feb. 15, 1991).

Fischer, T. A et al. "Activation of cGMP-dependent protein kinase Ibeta inhibits interleukin 2 release and proliferation of T cell receptor-stimulated human peripheral T cells," 20 U., Sopper, S., & Lohmann, S. M. (2001). J. Biol. Chem. 276, 5967-5974.

Forte L. R., "Guanylin regulatory peptides: structures, biological activities mediated by cyclic GMP and pathobiology," *Regul. Pept.* May 31, 1999;81(1-3):25-39.

Fukumoto, S. et al., "Distinct role of cAMP and cGMP in the cell cycle control of vascular smooth muscle cells: cGMP delays cell cycle transition through suppression of cyclin D1 and cyclin-dependent kinase 4 activation," *Circ. Res.* (1999) 85(11), 985-991.

Gadbois, D. M. et al. "Multiple kinase arrest points in the G1 phase of nontransformed mammalian cells are absent in transformed cells," *Proc. Natl. Acad. Sci. USA* (1992), 89(18), 8626-8630.

Giannella, R. A. et al., "*Escherichia coli* heat-stable enterotoxins, guanylins, and their receptors: what are they and what do they do?" *J. Lab. Clin. Med.* (1995), 125(2), 173-181.

Guarino, A. et al., "Small and large intestinal guanylate cyclase activity in children: effect of age and stimulation by *Escherichia coli* heat-stable enterotoxin," *Pediatr. Res.* (1987), 21(6), 551-555.

Grider J., "Interplay of VIP and nitric oxide in regulation of the descending relaxation phase of perstalsis," *Am. J. Physiol.* Feb. 1993;26(2 Pt 1)G334-40.

Hamra, F. K. et al., "Uroguanylin: structure and activity of a second endogenous peptide that stimulates intestinal guanylate cyclase" *Proc. Natl. Acad. Sci. USA* (1993), 90(22), 10464-10468.

Harrison, S. A et al., "Isolation and characterization of bovine cardiac muscle cGMP-inhibited phosphodiesterase: a receptor for new cardiotonic drugs," *Mol. Pharmaco.* (May 1986);29(5):506-14.

Hill. O et al., "A new human guanylate cyclase-activating peptide (GCAP-II, uroguanylin): precursor cDNA and colonic expression," *Biocim BioPhys. Acta* (1995) 1253 (2), 146-149.

Hill, D. R et al., "Health advice for international travel," *Ann. Intern. Med.* (1988), 108(6), 839-852.

Hood, J. et al., "Protein kinase G mediates vascular endothelial growth factor-induced Raf-1 activation and proliferation in human endothelial cells ," *J. Biol. Chem.* (1998), 273(36), 23504-23508.

Hughes, J. M. et al., "Role of cyclic GMP in the action of heat-stable enterotoxin of *Escherichia coli*,"*Nature* (1978), 271, 755-756.

Kent and Clark-Lewis, *Synthetic Peptides in Biology and Medicine*, p. 295-358 (Alitalo, K et al. Elsevier Science Publishers, Amsterdam, 1985).

Knoop, F. C. et al., "Pharmacologic action of *Escherichia coli* heat-stable (STa) enterotoxin ," *J. Pharmacol. Toxicol. Methods* (1992) 28(2), 67-72.

Larrick and Fry, "Recombinant antibodies," *Hum. Antibod. and hybridomas* (1991), 2(4):172-89.

Lucas, K. A. et al., "Guanylyl cyclases and signaling by cyclic GMP," *Pharmacol. Rev.* (2000), 52(3), 375-414.

Merrifield, "Solid Phase Peptide Synthesis. I. The Synthesis of a Tetrapeptide," *J. Am. Chem. Soc.* (1963) 15:2149-2154.

Miyazato, M. et al., "Uroguanylin gene expression in the alimentary tract and extra-gastrointestinal tissues,"*FEBS Lett.* (1996), 398 (2-3), 170-174.

Miyazato, M. et al., "Cloning and characterization of a cDNA encoding a precursor for human uroguanylin," *Biochem. Biophys Res. Commun.* (1996), 219 (2), 644-648.

Miyazato, M. et al., "Genomic structure and chromosomal localization of human uroguanylin.," *Genomics* (1997)43 (3), 359-365.

Moseley et al., "Isolation and nucleotide sequence determination of a gene encoding a heat-stable enterotoxin of *Escherichia coli*," *Infect Immun.* (1983) 39(3):1167-74.

Notterman, D. A. et al., "Transcriptional gene expression profiles of colorectal adenoma, adenocarcinoma, and normal tissue examined by oligonucleotide arrays," *Cancer Res.* (2001), 61(7), 3124-3130.

Neurath, H et al., *The Proteins*, vol. II, 3d Ed., p. 105-137,., Academic Press, New York , NY (1976).

Okamoto, K. et al., "Substitutions of cysteine residues of *Escherichia coli* heat-stable enterotoxin by oligonucleotide-directed mutagenesis," *Infec. Immun.* (1985), 55:2121-2125.

Parkinson, S. J. et al., "Interruption of *Escherichia coli* heat-stable enterotoxin-induced guanylyl cyclase signaling and associated chloride current in human intestinal cells by 2-chloroadenosine ," *J. Biol. Chem.* (1997), 272(2), 754-758.

Penman, I. D. et al., "Dietary calcium supplementation increases apoptosis in the distal murine colonic epithelium," *J. Clin. Pathol.* (2000), 53(4), 302-307.

Pitari, G. M. et al., "Guanylyl cyclase C agonists regulate progression through the cell cycle of human colon carcinoma cells.," *Proc. Natl. Acad. Sci. USA* (2001), 98(14), 7846-7851.

Qiu, W. et al., "Cyclic nucleotide-gated cation channels mediate sodium and calcium influx in rat colon," *Am. J. Physiol.* (2000) 278(2), C336-C343.

Rosado, J. A., "Cyclic nucleotides modulate store-mediated calcium entry through the activation of protein-tyrosine phosphatases and altered actin polymerization in human platelets," *J. Biol. Chem.* (2001) 276(19), 15666-15675.

Sauvage F.J. et al., "Primary structure and functional expression of the human receptor for *Escherichia coli* heat-stable enterotoxin," *Journal of Biol. Chemistry* (1991) 266(27):17912-8.

Sesink, A. L. et al., "Red meat and colon cancer: dietary haem-induced colonic cytotoxicity and epithelial hyperproliferation are inhibited by calcium ," *Carcinogenesis* (2001) 22(10), 1653-1659.

Schulz, S. et al., "Guanylyl cyclase is a heat-stable enterotoxin receptor," *Cell* (1990), 63(5), 941-948.

Shailubhai, K. et al., "Uroguanylin treatment suppresses polyp formation in the Apc(Min/+) mouse and induces apoptosis in human colon adenocarcinoma cells via cyclic GMP," *Cancer Res.* (2000) 60(18), 5151-5157.

Shimonishi, Y. et al., "Mode of disulfide bond formation of a heat-stable enterotoxin (STh) produced by a human strain of enterotoxigenic *Escherichia coli*," *FEBS Lett.* (1987), 215(1):165-170.

So and McCarthy et al. "Nucleotide sequence of the bacterial transposon Tn1681 encoding a heat-stable (ST) toxin and its identification in enterotoxigenic *Escherichia coli* strains ," *Proc. Natl. Acad. Sci USA* (1980), 77:4011-4015.

Stern, J. H. et al., "Control of the light-regulated current in rod photoreceptors by cyclic GMP, calcium, and I-cis-diltiazem," *Proc. Natl. Acad. Sci. USA* (1986) 83(4), 1163-1167.

Sugimoto, T. et al., "Atrial natriuretic peptide induces the expression of MKP-1, a mitogen-activated protein kinase phosphatase, in glomerular mesangial cells," *J. Biol. Chem.* (1996), 271(1), 544-547.

Thompson, W. J. et al., "Exisulind induction of apoptosis involves guanosine 3',5'-cyclic monophosphate phosphodiesterase inhibition, protein kinase G activation, and attenuated beta-catenin," *Cancer Res.* (2000), 60(13), 3338-3342.

Waldman, S.A. et al., "Influence of a glycine or proline substitution on the functional properties of a 14-amino-acid analog of *Escherichia coli* heat-stable enterotoxin," *Infect. Immun.* (1989) 57(8):2420-4.

Vaandrager et al., "Guanosine 3',5'-cyclic monophosphate-dependent protein kinase II mediates heat-stable enterotoxin-provoked chloride secretion in rat intestine," *Gastroenterology* (1997) 112(2), 437-443.

Vaandrager et al., "Guanylyl cyclase C is an N-linked glycoprotein receptor that accounts for multiple heat-stable enterotoxin-binding proteins in the intestine," *J. Biolog. Chem.* (1993) 268(3):2174-2179.

Vaandrager et al., "Differential role of cyclic GMP-dependent protein kinase II in ion transport in murine small intestine and colon ," *Gastroenterology* (2000),118(1), 108-114.

Waldman, S. A. et al., "Heterogeneity of guanylyl cyclase C expressed by human colorectal cancer cell lines in vitro," *Cancer Epidemiol. Biomarkers Prev.* (1998) 7(6), 505-514.

Wilmink, A. B. et al., "Overview of the epidemiology of colorectal cancer," *Dis. Colon Rectum* (1997)40(4), 483-493.

Winter et al., "Man-made antibodies," *Nature* (1990), 349(6307):293-299.

Yoshimura, S. et al., "Essential structure for full enterotoxigenic activity of heat-stable enterotoxin produced by enterotoxigenic *Escherichia coli*" *FEBS Lett.* (1985) 181(1):138-142.

Zufall, F. et al., "Cyclic nucleotide gated channels as regulators of CNS development and plasticity," *Curr. Opin. Neurobiol.* (1997), 7(3), 404-412.

Zhang, W. et al., "Interruption of transmembrane signaling as a novel antisecretory strategy to treat enterotoxigenic diarrhea ," *FASEB J.* (1999),13, 913-922.

Zingman, L. V. et al., "Signaling in channel/enzyme multimers: ATPase transitions in SUR module gate ATP-sensitive K+ conductance," *Neuron* (2001) 31, 233-245.

Waldman et al., "The *E coli* heat-stable enterotoxin receptor is a specific marker for metastatic colorectal cancer in extraintestinal tissues and blood," Clinical Pharmacology and Therapeutics (1997) 61(2):194.

* cited by examiner

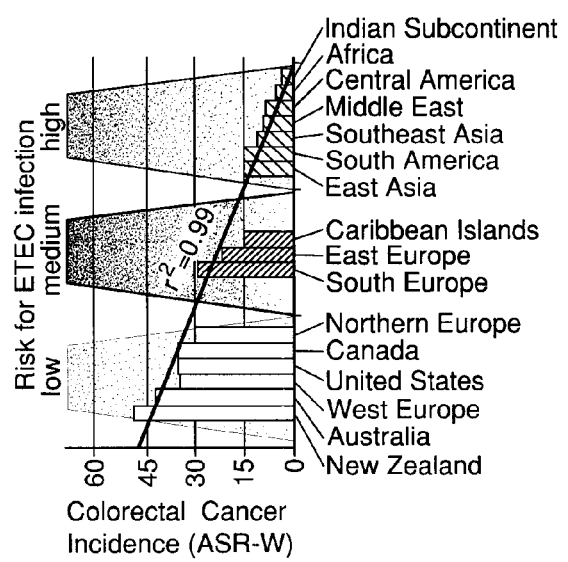
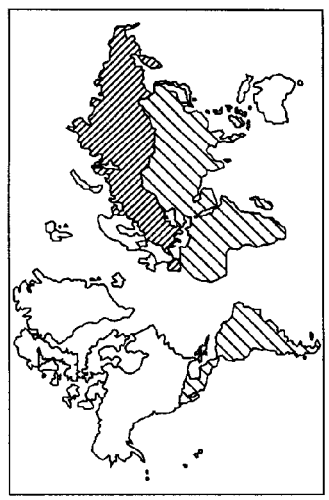
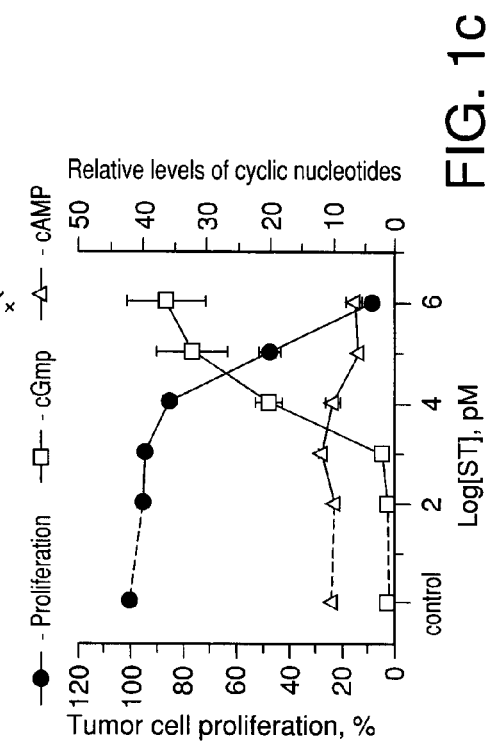
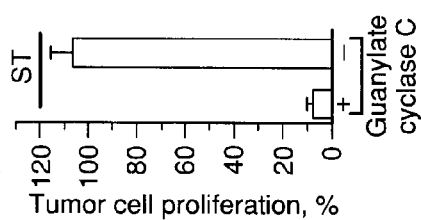
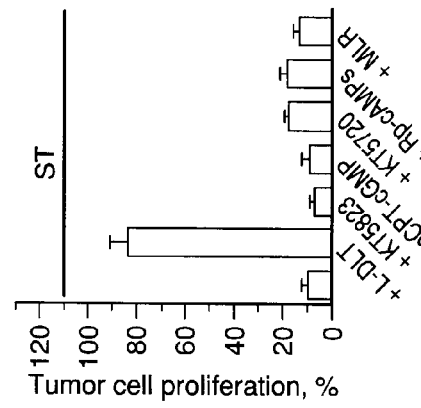

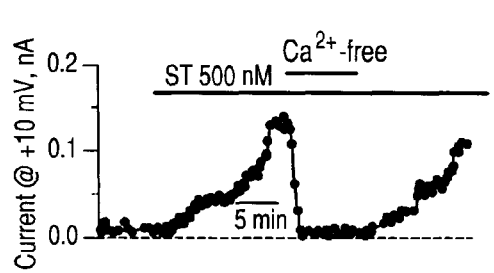
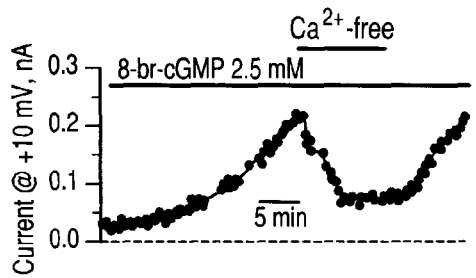
Fig. 2a   FIG. 2b
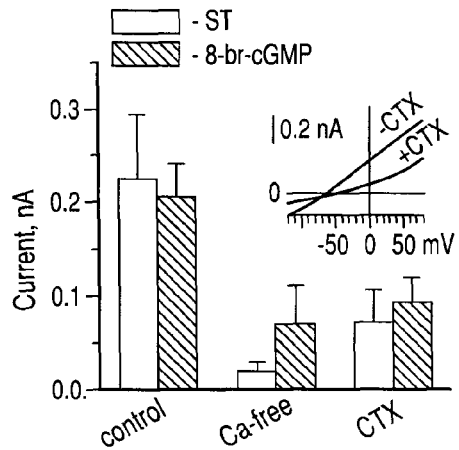
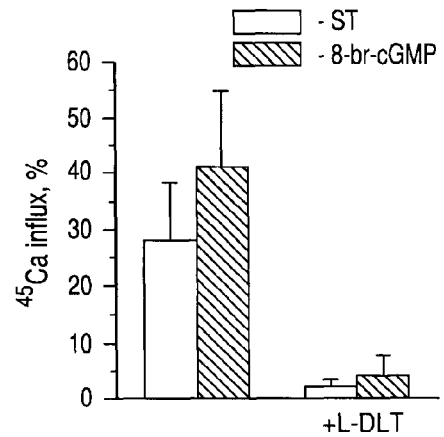
FIG. 2c   FIG. 2d
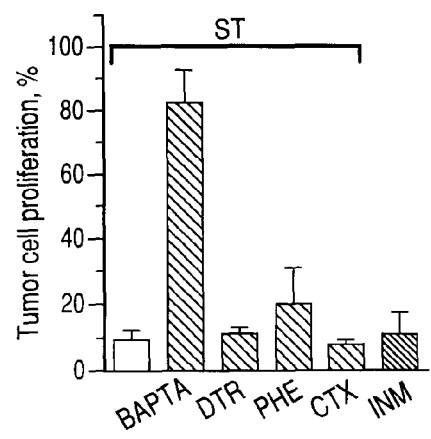
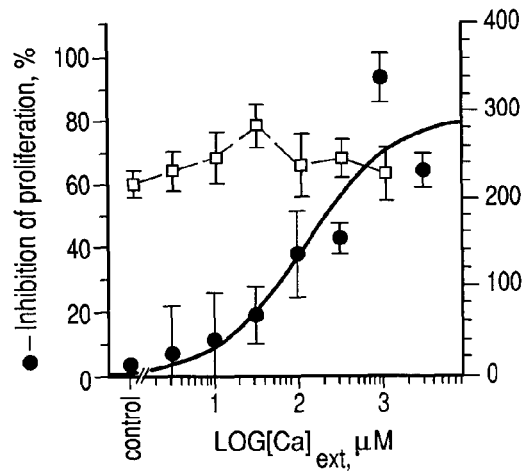
FIG. 2e   FIG. 2f

SEQUENCE LISTING

```
<160> NUMBER OF SEQ ID NOS: 56

<210> SEQ ID NO 1
<211> LENGTH: 57
<212> TYPE: DNA
<213> ORGANISM: Artificial Sequence
<220> FEATURE:
<223> OTHER INFORMATION: encodes heat stable toxin peptide of SEQ ID
      NO: 2
<220> FEATURE:
<221> NAME/KEY: CDS
<222> LOCATION: (1)...(57)

<400> SEQUENCE: 1 aac aac aca ttt tac tgc tgt gaa ctt tgt tgt aat cct gcc tgt gct      48
Asn Asn Thr Phe Tyr Cys Cys Glu Leu Cys Cys Asn Pro Ala Cys Ala
 1               5                  10                  15 gga tgt tat                                                          57
Gly Cys Tyr <210> SEQ ID NO 2
<211> LENGTH: 19
<212> TYPE: PRT
<213> ORGANISM: Artificial Sequence
<220> FEATURE:
<223> OTHER INFORMATION: heat stable toxin peptide Ia

<400> SEQUENCE: 2

Asn Asn Thr Phe Tyr Cys Cys Glu Leu Cys Cys Asn Pro Ala Cys Ala
 1               5                  10                  15

Gly Cys Tyr

<210> SEQ ID NO 3
<211> LENGTH: 18
<212> TYPE: PRT
<213> ORGANISM: Artificial Sequence
<220> FEATURE:
<223> OTHER INFORMATION: heat stable toxin peptide I*

<400> SEQUENCE: 3

Asn Thr Phe Tyr Cys Cys Glu Leu Cys Cys Tyr Pro Ala Cys Ala Gly
 1               5                  10                  15

Cys Asn
```

```
<210> SEQ ID NO 4
<211> LENGTH: 57
<212> TYPE: DNA
<213> ORGANISM: Artificial Sequence
<220> FEATURE:
<223> OTHER INFORMATION: encodes heat stable toxin peptide of SEQ ID
      NO: 5
<220> FEATURE:
<221> NAME/KEY: CDS
<222> LOCATION: (1)...(57)

<400> SEQUENCE: 4 aat agt agc aat tac tgc tgt gaa ttg tgt tgt aat cct gct tgt aac      48
Asn Ser Ser Asn Tyr Cys Cys Glu Leu Cys Cys Asn Pro Ala Cys Asn
 1               5                  10                  15 ggg tgc tat                                                          57
Gly Cys Tyr <210> SEQ ID NO 5
<211> LENGTH: 19
<212> TYPE: PRT
<213> ORGANISM: Artificial Sequence
<220> FEATURE:
<223> OTHER INFORMATION: heat stable toxin peptide Ib

<400> SEQUENCE: 5

Asn Ser Ser Asn Tyr Cys Cys Glu Leu Cys Cys Asn Pro Ala Cys Asn
 1               5                  10                  15

Gly Cys Tyr

<210> SEQ ID NO 6
<211> LENGTH: 15
<212> TYPE: PRT
<213> ORGANISM: Artificial Sequence
<220> FEATURE:
<223> OTHER INFORMATION: guanylin

<400> SEQUENCE: 6

Pro Asn Thr Cys Glu Ile Cys Ala Tyr Ala Ala Cys Thr Gly Cys
 1               5                  10                  15

<210> SEQ ID NO 7
<211> LENGTH: 18
<212> TYPE: PRT
<213> ORGANISM: Artificial Sequence
<220> FEATURE:
<223> OTHER INFORMATION: fragment of SEQ ID NO: 2

<400> SEQUENCE: 7

Asn Asn Thr Phe Tyr Cys Cys Glu Leu Cys Cys Asn Pro Ala Cys Ala
 1               5                  10                  15

Gly Cys

<210> SEQ ID NO 8
<211> LENGTH: 17
<212> TYPE: PRT
<213> ORGANISM: Artificial Sequence
<220> FEATURE:
<223> OTHER INFORMATION: fragment of SEQ ID NO: 2

<400> SEQUENCE: 8

Asn Thr Phe Tyr Cys Cys Glu Leu Cys Cys Asn Pro Ala Cys Ala Gly
 1               5                  10                  15

Cys
```

```
<210> SEQ ID NO 9
<211> LENGTH: 16
<212> TYPE: PRT
<213> ORGANISM: Artificial Sequence
<220> FEATURE:
<223> OTHER INFORMATION: fragment of SEQ ID NO: 2

<400> SEQUENCE: 9

Thr Phe Tyr Cys Cys Glu Leu Cys Cys Asn Pro Ala Cys Ala Gly Cys
 1               5                  10                  15

<210> SEQ ID NO 10
<211> LENGTH: 15
<212> TYPE: PRT
<213> ORGANISM: Artificial Sequence
<220> FEATURE:
<223> OTHER INFORMATION: fragment of SEQ ID NO: 2

<400> SEQUENCE: 10

Phe Tyr Cys Cys Glu Leu Cys Cys Asn Pro Ala Cys Ala Gly Cys
 1               5                  10                  15

<210> SEQ ID NO 11
<211> LENGTH: 14
<212> TYPE: PRT
<213> ORGANISM: Artificial Sequence
<220> FEATURE:
<223> OTHER INFORMATION: fragment of SEQ ID NO: 2

<400> SEQUENCE: 11

Tyr Cys Cys Glu Leu Cys Cys Asn Pro Ala Cys Ala Gly Cys
 1               5                  10

<210> SEQ ID NO 12
<211> LENGTH: 13
<212> TYPE: PRT
<213> ORGANISM: Artificial Sequence
<220> FEATURE:
<223> OTHER INFORMATION: fragment of SEQ ID NO: 2

<400> SEQUENCE: 12

Cys Cys Glu Leu Cys Cys Asn Pro Ala Cys Ala Gly Cys
 1               5                  10

<210> SEQ ID NO 13
<211> LENGTH: 18
<212> TYPE: PRT
<213> ORGANISM: Artificial Sequence
<220> FEATURE:
<223> OTHER INFORMATION: fragment of SEQ ID NO: 2

<400> SEQUENCE: 13

Asn Thr Phe Tyr Cys Cys Glu Leu Cys Cys Asn Pro Ala Cys Ala Gly
 1               5                  10                  15

Cys Tyr

<210> SEQ ID NO 14
<211> LENGTH: 17
<212> TYPE: PRT
<213> ORGANISM: Artificial Sequence
<220> FEATURE:
<223> OTHER INFORMATION: fragment of SEQ ID NO: 2

<400> SEQUENCE: 14

Thr Phe Tyr Cys Cys Glu Leu Cys Cys Asn Pro Ala Cys Ala Gly Cys
 1               5                  10                  15
```

Tyr

<210> SEQ ID NO 15
<211> LENGTH: 16
<212> TYPE: PRT
<213> ORGANISM: Artificial Sequence
<220> FEATURE:
<223> OTHER INFORMATION: fragment of SEQ ID NO: 2

<400> SEQUENCE: 15

Phe Tyr Cys Cys Glu Leu Cys Cys Asn Pro Ala Cys Ala Gly Cys Tyr
 1               5                  10                  15

<210> SEQ ID NO 16
<211> LENGTH: 15
<212> TYPE: PRT
<213> ORGANISM: Artificial Sequence
<220> FEATURE:
<223> OTHER INFORMATION: fragment of SEQ ID NO: 2

<400> SEQUENCE: 16

Tyr Cys Cys Glu Leu Cys Cys Asn Pro Ala Cys Ala Gly Cys Tyr
 1               5                  10                  15

<210> SEQ ID NO 17
<211> LENGTH: 14
<212> TYPE: PRT
<213> ORGANISM: Artificial Sequence
<220> FEATURE:
<223> OTHER INFORMATION: fragment of SEQ ID NO: 2

<400> SEQUENCE: 17

Cys Cys Glu Leu Cys Cys Asn Pro Ala Cys Ala Gly Cys Tyr
 1               5                  10

<210> SEQ ID NO 18
<211> LENGTH: 17
<212> TYPE: PRT
<213> ORGANISM: Artificial Sequence
<220> FEATURE:
<223> OTHER INFORMATION: fragment of SEQ ID NO: 3

<400> SEQUENCE: 18

Asn Thr Phe Tyr Cys Cys Gly Leu Cys Cys Tyr Pro Ala Cys Ala Gly
 1               5                  10                  15

Cys

<210> SEQ ID NO 19
<211> LENGTH: 16
<212> TYPE: PRT
<213> ORGANISM: Artificial Sequence
<220> FEATURE:
<223> OTHER INFORMATION: fragment of SEQ ID NO: 3

<400> SEQUENCE: 19

Thr Phe Tyr Cys Cys Glu Leu Cys Cys Tyr Pro Ala Cys Ala Gly Cys
 1               5                  10                  15

<210> SEQ ID NO 20
<211> LENGTH: 15
<212> TYPE: PRT
<213> ORGANISM: Artificial Sequence
<220> FEATURE:
<223> OTHER INFORMATION: fragment of SEQ ID NO: 3

<400> SEQUENCE: 20

Phe Tyr Cys Cys Glu Leu Cys Cys Tyr Pro Ala Cys Ala Gly Cys

<210> SEQ ID NO 21
<211> LENGTH: 14
<212> TYPE: PRT
<213> ORGANISM: Artificial Sequence
<220> FEATURE:
<223> OTHER INFORMATION: fragment of SEQ ID NO: 3

<400> SEQUENCE: 21

Tyr Cys Cys Glu Leu Cys Cys Tyr Pro Ala Cys Ala Gly Cys
1               5                   10

<210> SEQ ID NO 22
<211> LENGTH: 13
<212> TYPE: PRT
<213> ORGANISM: Artificial Sequence
<220> FEATURE:
<223> OTHER INFORMATION: fragment of SEQ ID NO: 3

<400> SEQUENCE: 22

Cys Cys Glu Leu Cys Cys Tyr Pro Ala Cys Ala Gly Cys
1               5                   10

<210> SEQ ID NO 23
<211> LENGTH: 17
<212> TYPE: PRT
<213> ORGANISM: Artificial Sequence
<220> FEATURE:
<223> OTHER INFORMATION: fragment of SEQ ID NO: 3

<400> SEQUENCE: 23

Thr Phe Tyr Cys Cys Glu Leu Cys Cys Tyr Pro Ala Cys Ala Gly Cys
1               5                   10                  15
Asn

<210> SEQ ID NO 24
<211> LENGTH: 16
<212> TYPE: PRT
<213> ORGANISM: Artificial Sequence
<220> FEATURE:
<223> OTHER INFORMATION: fragment of SEQ ID NO: 3

<400> SEQUENCE: 24

Phe Tyr Cys Cys Glu Leu Cys Cys Tyr Pro Ala Cys Ala Gly Cys Asn
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: fragment of SEQ ID NO: 3

<400> SEQUENCE: 25

Tyr Cys Cys Glu Leu Cys Cys Tyr Pro Ala Cys Ala Gly Cys Asn
1               5                   10                  15

<210> SEQ ID NO 26
<211> LENGTH: 14
<212> TYPE: PRT
<213> ORGANISM: Artificial Sequence
<220> FEATURE:
<223> OTHER INFORMATION: fragment of SEQ ID NO: 3

<400> SEQUENCE: 26

Cys Cys Glu Leu Cys Cys Tyr Pro Ala Cys Ala Gly Cys Asn

<210> SEQ ID NO 27
<211> LENGTH: 18
<212> TYPE: PRT
<213> ORGANISM: Artificial Sequence
<220> FEATURE:
<223> OTHER INFORMATION: fragment of SEQ ID NO: 5

<400> SEQUENCE: 27

Asn Ser Ser Asn Tyr Cys Cys Glu Leu Cys Cys Asn Pro Ala Cys Thr
 1               5                  10                  15
Gly Cys

<210> SEQ ID NO 28
<211> LENGTH: 17
<212> TYPE: PRT
<213> ORGANISM: Artificial Sequence
<220> FEATURE:
<223> OTHER INFORMATION: fragment of SEQ ID NO: 5

<400> SEQUENCE: 28

Ser Ser Asn Tyr Cys Cys Glu Leu Cys Cys Asn Pro Ala Cys Thr Gly
 1               5                  10                  15
Cys

<210> SEQ ID NO 29
<211> LENGTH: 16
<212> TYPE: PRT
<213> ORGANISM: Artificial Sequence
<220> FEATURE:
<223> OTHER INFORMATION: fragment of SEQ ID NO: 5

<400> SEQUENCE: 29

Ser Asn Tyr Cys Cys Glu Leu Cys Cys Asn Pro Ala Cys Thr Gly Cys
 1               5                  10                  15

<210> SEQ ID NO 30
<211> LENGTH: 15
<212> TYPE: PRT
<213> ORGANISM: Artificial Sequence
<220> FEATURE:
<223> OTHER INFORMATION: fragment of SEQ ID NO: 5

<400> SEQUENCE: 30

Asn Tyr Cys Cys Glu Leu Cys Cys Asn Pro Ala Cys Thr Gly Cys
 1               5                  10                  15

<210> SEQ ID NO 31
<211> LENGTH: 14
<212> TYPE: PRT
<213> ORGANISM: Artificial Sequence
<220> FEATURE:
<223> OTHER INFORMATION: fragment of SEQ ID NO: 5

<400> SEQUENCE: 31

Tyr Cys Cys Glu Leu Cys Cys Asn Pro Ala Cys Thr Gly Cys
 1               5                  10

<210> SEQ ID NO 32
<211> LENGTH: 13
<212> TYPE: PRT
<213> ORGANISM: Artificial Sequence
<220> FEATURE:
<223> OTHER INFORMATION: fragment of SEQ ID NO: 5

<400> SEQUENCE: 32

```
Cys Cys Glu Leu Cys Cys Asn Pro Ala Cys Thr Gly Cys
1               5                   10
```

<210> SEQ ID NO 33
<211> LENGTH: 18
<212> TYPE: PRT
<213> ORGANISM: Artificial Sequence
<220> FEATURE:
<223> OTHER INFORMATION: fragment of SEQ ID NO: 5

<400> SEQUENCE: 33

```
Ser Ser Asn Tyr Cys Cys Glu Leu Cys Cys Asn Pro Ala Cys Thr Gly
1               5                   10                  15

Cys Tyr
```

<210> SEQ ID NO 34
<211> LENGTH: 17
<212> TYPE: PRT
<213> ORGANISM: Artificial Sequence
<220> FEATURE:
<223> OTHER INFORMATION: fragment of SEQ ID NO: 5

<400> SEQUENCE: 34

```
Ser Asn Tyr Cys Cys Glu Leu Cys Cys Asn Pro Ala Cys Thr Gly Cys
1               5                   10                  15

Tyr
```

<210> SEQ ID NO 35
<211> LENGTH: 16
<212> TYPE: PRT
<213> ORGANISM: Artificial Sequence
<220> FEATURE:
<223> OTHER INFORMATION: fragment of SEQ ID NO: 5

<400> SEQUENCE: 35

```
Asn Tyr Cys Cys Glu Leu Cys Cys Asn Pro Ala Cys Thr Gly Cys Tyr
1               5                   10                  15
```

<210> SEQ ID NO 36
<211> LENGTH: 15
<212> TYPE: PRT
<213> ORGANISM: Artificial Sequence
<220> FEATURE:
<223> OTHER INFORMATION: fragment of SEQ ID NO: 5

<400> SEQUENCE: 36

```
Tyr Cys Cys Glu Leu Cys Cys Asn Pro Ala Cys Thr Gly Cys Tyr
1               5                   10                  15
```

<210> SEQ ID NO 37
<211> LENGTH: 14
<212> TYPE: PRT
<213> ORGANISM: Artificial Sequence
<220> FEATURE:
<223> OTHER INFORMATION: fragment of SEQ ID NO: 5

<400> SEQUENCE: 37

```
Cys Cys Glu Leu Cys Cys Asn Pro Ala Cys Thr Gly Cys Tyr
1               5                   10
```

<210> SEQ ID NO 38
<211> LENGTH: 18
<212> TYPE: PRT
<213> ORGANISM: Artificial Sequence
<220> FEATURE:
<223> OTHER INFORMATION: derivative

```
<400> SEQUENCE: 38

Asn Thr Phe Tyr Cys Cys Glu Leu Cys Cys Asn Pro Ala Cys Ala Gly
  1               5                  10                  15

Cys Tyr

<210> SEQ ID NO 39
<211> LENGTH: 18
<212> TYPE: PRT
<213> ORGANISM: Artificial Sequence
<220> FEATURE:
<223> OTHER INFORMATION: derivative

<400> SEQUENCE: 39

Asn Thr Phe Tyr Cys Cys Glu Leu Cys Cys Ala Pro Ala Cys Ala Gly
  1               5                  10                  15

Cys Tyr

<210> SEQ ID NO 40
<211> LENGTH: 18
<212> TYPE: PRT
<213> ORGANISM: Artificial Sequence
<220> FEATURE:
<223> OTHER INFORMATION: derivative

<400> SEQUENCE: 40

Asn Thr Phe Tyr Cys Cys Glu Leu Cys Cys Asn Ala Ala Cys Ala Gly
  1               5                  10                  15

Cys Tyr

<210> SEQ ID NO 41
<211> LENGTH: 17
<212> TYPE: PRT
<213> ORGANISM: Artificial Sequence
<220> FEATURE:
<223> OTHER INFORMATION: derivative

<400> SEQUENCE: 41

Asn Thr Phe Tyr Cys Cys Glu Leu Cys Cys Asn Pro Ala Cys Ala Gly
  1               5                  10                  15

Cys

<210> SEQ ID NO 42
<211> LENGTH: 15
<212> TYPE: PRT
<213> ORGANISM: Artificial Sequence
<220> FEATURE:
<223> OTHER INFORMATION: derivative

<400> SEQUENCE: 42

Tyr Cys Cys Glu Leu Cys Cys Asn Pro Ala Cys Ala Gly Cys Tyr
  1               5                  10                  15

<210> SEQ ID NO 43
<211> LENGTH: 14
<212> TYPE: PRT
<213> ORGANISM: Artificial Sequence
<220> FEATURE:
<223> OTHER INFORMATION: derivative

<400> SEQUENCE: 43

Tyr Cys Cys Glu Leu Cys Cys Asn Pro Ala Cys Ala Gly Cys
  1               5                  10
```

```
<210> SEQ ID NO 44
<211> LENGTH: 14
<212> TYPE: PRT
<213> ORGANISM: Artificial Sequence
<220> FEATURE:
<223> OTHER INFORMATION: derivative

<400> SEQUENCE: 44

Cys Cys Glu Leu Cys Cys Asn Pro Ala Cys Ala Gly Cys Tyr
 1               5                  10

<210> SEQ ID NO 45
<211> LENGTH: 13
<212> TYPE: PRT
<213> ORGANISM: Artificial Sequence
<220> FEATURE:
<223> OTHER INFORMATION: derivative

<400> SEQUENCE: 45

Cys Cys Glu Leu Cys Cys Asn Pro Ala Cys Ala Gly Cys
 1               5                  10

<210> SEQ ID NO 46
<211> LENGTH: 25
<212> TYPE: PRT
<213> ORGANISM: Artificial Sequence
<220> FEATURE:
<223> OTHER INFORMATION: derivative

<400> SEQUENCE: 46

Gln Ala Cys Asp Pro Pro Ser Pro Ala Glu Val Cys Cys Asp Val
 1               5                  10                  15

Cys Cys Asn Pro Ala Cys Ala Gly Cys
            20                  25

<210> SEQ ID NO 47
<211> LENGTH: 16
<212> TYPE: PRT
<213> ORGANISM: Artificial Sequence
<220> FEATURE:
<223> OTHER INFORMATION: derivative

<400> SEQUENCE: 47

Ile Asp Cys Cys Ile Cys Cys Asn Pro Ala Cys Phe Gly Cys Leu Asn
 1               5                  10                  15

<210> SEQ ID NO 48
<211> LENGTH: 18
<212> TYPE: PRT
<213> ORGANISM: Artificial Sequence
<220> FEATURE:
<223> OTHER INFORMATION: derivative

<400> SEQUENCE: 48

Ser Ser Asp Trp Asp Cys Cys Asp Val Cys Cys Asn Pro Ala Cys Ala
 1               5                  10                  15

Gly Cys

<210> SEQ ID NO 49
<211> LENGTH: 19
<212> TYPE: PRT
<213> ORGANISM: Artificial Sequence
<220> FEATURE:
<223> OTHER INFORMATION: derivative

<400> SEQUENCE: 49

Asn Ser Ser Asn Tyr Cys Cys Glu Leu Cys Cys Tyr Pro Ala Cys Thr
```

```
                1               5                  10                  15
Gly Cys Tyr

<210> SEQ ID NO 50
<211> LENGTH: 13
<212> TYPE: PRT
<213> ORGANISM: Artificial Sequence
<220> FEATURE:
<223> OTHER INFORMATION: derivative

<400> SEQUENCE: 50

Cys Cys Asp Val Cys Cys Asn Pro Ala Cys Thr Gly Cys
1               5                  10

<210> SEQ ID NO 51
<211> LENGTH: 14
<212> TYPE: PRT
<213> ORGANISM: Artificial Sequence
<220> FEATURE:
<223> OTHER INFORMATION: derivative

<400> SEQUENCE: 51

Cys Cys Asp Val Cys Cys Tyr Pro Ala Cys Thr Gly Cys Tyr
1               5                  10

<210> SEQ ID NO 52
<211> LENGTH: 14
<212> TYPE: PRT
<213> ORGANISM: Artificial Sequence
<220> FEATURE:
<223> OTHER INFORMATION: derivative

<400> SEQUENCE: 52

Cys Cys Asp Leu Cys Cys Asn Pro Ala Cys Ala Gly Cys Tyr
1               5                  10

<210> SEQ ID NO 53
<211> LENGTH: 14
<212> TYPE: PRT
<213> ORGANISM: Artificial Sequence
<220> FEATURE:
<223> OTHER INFORMATION: derivative

<400> SEQUENCE: 53

Cys Cys Gln Leu Cys Cys Asn Pro Ala Cys Thr Gly Cys Tyr
1               5                  10

<210> SEQ ID NO 54
<211> LENGTH: 15
<212> TYPE: PRT
<213> ORGANISM: Homo sapiens

<400> SEQUENCE: 54

Pro Gly Thr Cys Glu Ile Cys Ala Tyr Ala Ala Cys Thr Gly Cys
1               5                  10                  15

<210> SEQ ID NO 55
<211> LENGTH: 106
<212> TYPE: PRT
<213> ORGANISM: Rattus norvegicus

<400> SEQUENCE: 55

Met Ser Gly Ser Gln Leu Trp Ala Ala Val Leu Leu Leu Val Leu
1               5                  10                  15

Gln Ser Ala Gln Gly Val Tyr Ile Lys Tyr His Gly Phe Gln Val Gln
            20                  25                  30
```

```
Leu Glu Ser Val Lys Lys Leu Asn Glu Leu Glu Lys Gln Met Ser
        35                  40                  45

Asp Pro Gln Gln Lys Ser Gly Leu Leu Pro Asp Val Cys Tyr Asn
    50                  55                  60

Pro Ala Leu Pro Leu Asp Leu Gln Pro Val Cys Ala Ser Gln Glu Ala
65              70                  75                      80

Ala Ser Thr Phe Lys Ala Leu Arg Thr Ile Ala Thr Asp Glu Cys Glu
            85                  90                  95

Leu Cys Ile Asn Val Ala Cys Thr Gly Cys
            100             105

<210> SEQ ID NO 56
<211> LENGTH: 112
<212> TYPE: PRT
<213> ORGANISM: Homo sapiens

<400> SEQUENCE: 56

Met Gly Cys Arg Ala Ala Ser Gly Leu Leu Pro Gly Val Ala Val Val
1               5                   10                  15

Leu Leu Leu Leu Leu Gln Ser Thr Gln Ser Val Tyr Ile Gln Tyr Gln
            20                  25                  30

Gly Phe Arg Val Gln Leu Glu Ser Met Lys Lys Leu Ser Asp Leu Glu
            35                  40                  45

Ala Gln Trp Ala Pro Ser Pro Arg Leu Gln Ala Gln Ser Leu Leu Pro
    50                  55                  60

Ala Val Cys His His Pro Ala Leu Pro Gln Asp Leu Gln Pro Val Cys
65              70                  75                      80

Ala Ser Gln Glu Ala Ser Ser Ile Phe Lys Thr Leu Arg Thr Ile Ala
            85                  90                  95

Asn Asp Asp Cys Glu Leu Cys Val Asn Val Ala Cys Thr Gly Cys Leu
            100                 105                 110
```

USE OF GCC LIGANDS

FIELD OF THE INVENTION

The present invention relates to methods of inhibiting proliferation of human colorectal, gastric and esophageal cells including: primary and metastasized human colorectal cancer cells, primary and metastasized human gastric cancer cells, and primary and metastasized human esophageal cancer cells. The present invention relates to methods of treating individuals who have diseases that effect colorectal, gastric and esophageal cells including colorectal, gastric and esophageal cancer. The present invention relates to improved methods of enhancing the therapeutic efficacy of existing methods of treating gastric, esophageal and colorectal cancers. The present invention relates to methods of increasing the number of ST receptors on the surface of human colorectal cells including metastasized human colorectal cancer cells. The present invention relates to methods of inhibiting the development of colorectal, gastric and esophageal cancer.

BACKGROUND OF THE INVENTION

The apical brush border membranes of normal mucosal cells lining the small and large intestine express a specific receptor, guanylyl cyclase C (gcC, hereinafter "ST receptor"). ST receptors are unique in that they are localized in the apical brush border membranes of normal cells lining the intestinal tract. Indeed, they are not found in any other normal cell type in placental mammals. It has been shown that normal gastric and esophageal cells do not express the ST receptor. The discovery has been made that primary and metastatic gastric and esophageal cancer cells express the ST receptor. In addition, ST receptor transcription products, such as mRNAs for the ST receptor protein and the ST receptor mRNA splice variant CRCA-1 are markers for gastric and esophageal cancer cells.

The ST receptors located in the lining of the small and large intestine are almost exclusively localized to the apical membranes, with little being found in the basolateral membranes on the sides of intestinal cells. Of significance is the fact that mucosal cells lining the intestine are joined together by tight junctions which form a barrier against the passage of intestinal contents into the blood stream and components of the blood stream into the intestinal lumen. Therefore, the apical location of ST receptors isolates these receptors from the circulatory system so that they may be considered to exist "outside the body" and the rest of the body is considered "outside the intestinal tract." Compositions administered "outside the intestinal tract" are maintained apart and segregated from the only cells which normally express ST receptors.

*E. coli* produce a small heat-stable toxin (ST) that is responsible for endemic diarrhea in developing countries and travelers diarrhea. This toxin induces intestinal secretion by binding to ST receptor in the apical brush border membranes of the mucosal cells lining the small and large intestine. Binding of toxin to these receptors triggers a cascade of biochemical reactions in the apical membrane of these cells resulting in the production of a signal which induces intestinal cells to secrete fluids and electrolytes, resulting in diarrhea. Two homologous peptides to ST are guanylin and uroguanylin, both of which are produced locally in the intestine.

The discovery that a large proportion of metastasized colorectal cells, and primary and metastatic gastric and esophageal cancer cells, including those found in liver, lung, bone, brain, nodes and peritoneum tissues, express ST receptors on their cell surfaces, even at highly undifferentiated stages gave rise to several inventions. Given that ST receptor expression is generally tissue-specific to normal cells lining the inside of the colon, the discovery of expression of ST receptors on the surfaces of metastatic colorectal tumor cells, as well as primary and metastatic gastric and esophageal cancer cells, provides a target for delivering imaging and therapeutic agents to these cells and provides a means for detecting and identifying cells of colorectal, gastric and esophageal origin in samples.

U.S. Pat. Nos. 5,518,888, 5,879,656, 6,060,037, and 6,268,159, which are each incorporated herein by reference, describe technologies which target metastasized colorectal tumor cells using compounds that specifically bind to ST receptors. Compounds which bind to ST receptors and which are either detectable or therapeutically active are administered to an individual parenterally. The compounds localize to the metastasized colorectal tumor cells through their affinity to ST receptors expressed by the cells.

U.S. Pat. Nos. 5,601,990, 5,731,159, 5,928,873, and 6,060,037, which are each incorporated herein by reference, describe technologies which detect ST receptor expression in extraintestinal samples as a means of detecting the presence of metastasized colorectal tumor cells. ST receptors and transcription products encoding ST receptors serve as molecular markers whose presence in extraintestinal samples indicates metastasized colorectal tumor cells and tumors of colorectal origin. ST receptor protein and nucleic acid molecules encoding ST receptor protein are detected in various ways such as, for example, immunoassays and PCR assays.

In addition to its use for targeting in in vivo therapeutics and diagnostic/imaging protocols as well as its use for targeting in in vitro diagnostic protocols, the tissue specific expression of ST receptor in cells of colorectal origin has also been exploited in methods and compositions for drug delivery, for example gene therapy. Cells that express ST receptor, i.e. cells of colorectal origin, including normal as well as cancer cells or primary and metastatic gastric and esophageal cells, can be specifically targeted. U.S. Pat. No. 5,962,220 and U.S. Pat. No. 6,087,109, which is incorporated herein by reference, describes the use of compounds which bind to ST receptors such as native ST or other ST receptor binding ligands, as ST receptor binding moieties used to deliver nucleic acid molecules such as antisense agents to colorectal cells by targeting ST receptors which are expressed by such cells.

Moreover, vaccines have been designed which induce an immune response against ST receptors and thus can be used to prophylactically and/or therapeutically immunize an individual against metastasized colorectal cancer. PCT application PCT/US97/07565, which is incorporated herein by reference, describes such vaccines and the uses therefor.

U.S. application Ser. No. 819,249 filed Mar. 27, 2000 and published Oct. 11, 2001 as U.S. Application Publication Number 20010029019, which is incorporated herein by reference, describes using ST receptor (GCC) as a marker for detection of Gastric and Esophageal Cancer and as a target for delivery of imaging and therapeutic agents against Gastric and Esophageal Cancer cells.

Moreover, vaccines have been designed which induce an immune response against ST receptors and thus can be used to prophylactically and/or therapeutically immunize an individual against metastasized colorectal cancer. PCT application PCT/US97/07565, which is incorporated herein by reference, describes such vaccines and the uses therefor.

There remains a need for improved methods of inhibiting the proliferation of colorectal, gastric and esophageal cancer cells. There remains a need for improved methods of inhibiting primary colorectal, gastric and esophageal cancer cells from metastasizing and metastasized colorectal, gastric and esophageal cancer cells from further metastasizing. There remains a need for improved methods of treating primary and metastasized colorectal, gastric and esophageal cancer in vivo. There remains a need for methods of inhibiting the development of colorectal, gastric and esophageal cancer from polyps and precacerous lesions in vivo. There remains a need for improved in vitro methods of and reagents and kits for treating metastasized colorectal and primary and metastatic gastric and esophageal cancer. There remains an need for improved methods of and compositions for treating, imaging and detecting metastasized colorectal cancer in vivo. There remains an need for improved in vitro methods of and reagents and kits for diagnosing metastasized colorectal cancer and of identifying cancer as being of colorectal origin. There remains an need for improved methods of delivering compounds to colorectal cells. There remains a need for improved vaccines for preventing and treating metastasized colorectal cancer.

SUMMARY OF THE INVENTION

The present invention relates to in vivo and in vitro methods of inhibiting the proliferation of human colorectal, gastric and esophageal cancer cells.

The present invention further relates to methods of administering to an individual an effective amount of ST receptor binding agent for an effective amount of time to inhibit the of proliferation of metastasized human colorectal cancer cells and primary and metastatic human gastric and human esophageal cancer cells.

The present invention relates to methods of inhibiting the proliferation of metastasized colorectal, and primary and metastasized gastric and esophageal cells in an individual. The methods comprise the step of administering to the individual an amount of an ST receptor ligand sufficient to result in an inhibition of proliferation of human metastasized colorectal, and primary and metastasized gastric and esophageal cancer cells. The ST receptor ligand is administered to the individual in such a manner as to provide a sufficient number of ST receptor ligand molecules to come into contact with ST receptor proteins on the surface of the colorectal, gastric and esophageal cells in the individual for a sufficient time to result in an inhibition of the proliferation of such cells.

The present invention relates to methods of treating an individual identified as having metastatic colorectal, or primary or metastatic gastric or esophageal cancer by inhibiting the proliferation of metastasized colorectal cancer cells in an individual who has metastasized colorectal cancer or primary or metastasized gastric or esophageal cancer. The methods comprise the step of administering to the individual an amount of an ST receptor ligand sufficient to result in an inhibition of the proliferation of metastatic colorectal cancer cells or primary or metastatic gastric or esophageal cancer cells. The ST receptor ligand is administered to the individual in such a manner as to provide a sufficient number of ST receptor ligand molecules to come into contact with ST receptor proteins on the surface of the metastasized colorectal and primary and metastasized gastric and esophageal cancer cells in the individual for a sufficient time to result in an inhibition of the proliferation of the colorectal, gastric and esophageal cancer cells or to induce a therapeutic effect in the individual. This method may be followed by a further step of administering an ST receptor ligand-therapeutic agent conjugate.

The present invention relates to pharmaceutical compositions that comprise sterile, pyrogen free ST receptor ligand and a pharmaceutically acceptable carrier or diluent. The compositions contain an amount of ST receptor ligand effective to have a therapeutic effect in the treatment of cancer. The pharmaceutical compositions may be formulated for delivery such that the patient has a minimum titer of ST receptor ligand over a period of time sufficient to have a therapeutic benefit.

The present invention relates to methods of treating an individual who has metastasized colorectal cancer, as well as primary and metastasized gastric or esophageal cancer. The methods comprise the steps of administering an effective amount of ST receptor ligand to an individual in a therapeutic pharmaceutical composition for a period of time sufficient to result in an inhibition of the proliferation of metastasized colorectal or primary or metastasized gastric or esophageal cancer cells. The ST receptor ligand is administered to the individual in such a manner as to provide a sufficient number of ST receptor ligand molecules to come into contact with ST receptor proteins on the surface of the metastasized colorectal and primary and metastasized gastric and esophageal cancer cells in the individual for a sufficient time to result in an inhibition of proliferation or to cause a therapeutic effect in the individual. This method may be followed by a further step of administering a cell-division phase-specific therapeutic agent. This method also may be followed by alternating treatment steps using different phase-specific therapeutic agents.

The present invention relates to methods of treating an individual who has metastasized colorectal cancer, as well as primary and metastasized gastric or esophageal cancer. A pretreatment step of increasing the expression of ST receptor proteins on the surface of such cells may be performed in order to increase the number of ST receptor proteins expressed on the surface of the cells. This step may be followed by the method of the present invention directed to inhibiting the proliferation of such cells. The methods comprise the steps of administering an effective amount of ST receptor ligand to an individual in a therapeutic pharmaceutical composition for a period of time sufficient to result in an inhibition of the proliferation of metastasized colorectal or primary or metastasized gastric or esophageal cancer cells. The ST receptor ligand is administered to the individual in such a manner as to provide a sufficient number of ST receptor ligand molecules to come into contact with ST receptor proteins on the surface of the metastasized colorectal and primary and metastasized gastric and esophageal cancer cells in the individual for a sufficient time to result in an inhibition of proliferation or to cause a therapeutic effect in the individual.

The present invention relates to in vivo and in vitro methods of increasing the number of ST receptors on the surface of human colorectal cells.

The present invention further relates to methods of administering to an individual an effective amount of ST receptor binding agent for an effective amount of time to induce an increase in the number of ST receptors on the surface of metastasized human colorectal cancer cells.

The present invention relates to methods of increasing the number of ST receptor molecules on the surface of a colorectal cell in an individual. The methods comprise the step of administering to the individual an amount of an ST receptor ligand sufficient to result in an increase in the presence of ST receptor protein on the surface of the cell. The ST receptor ligand is administered to the individual in such a manner to provide a sufficient number of ST receptor ligand molecules to come into contact with ST receptor proteins on the surface of the colorectal cell in the individual for a sufficient time to result in an increase in the presence of ST receptor protein on the surface of the cell.

The present invention relates to methods of increasing the number of ST receptor molecules on the surface of a metastasized colorectal cancer cell in an individual who has metastasized colorectal cancer. The methods comprise the step of administering to the individual an amount of an ST receptor ligand sufficient to result in an increase in the presence of ST receptor protein on the surface of the cell. The ST receptor ligand is administered to the individual in such a manner to provide a sufficient number of ST receptor ligand molecules to come into contact with ST receptor proteins on the surface of the metastasized colorectal cancer cell in the individual for a sufficient time to result in an increase in the presence of ST receptor protein on the surface of the cell.

The present invention relates to pharmaceutical compositions that comprise sterile, pyrogen free ST receptor ligand and a pharmaceutically acceptable carrier or diluent. The compositions contain at least 0.6 nM of ST receptor ligand.

The present invention relates to methods of treating an individual who has metastasized colorectal cancer. The methods comprise the steps of increasing the number of ST receptor molecules on the surface of a metastasized colorectal cancer cell in the individual and then administering a therapeutic pharmaceutical composition that comprises components which target ST receptors for delivery of a therapeutic agent to the individual. The number of ST receptor molecules on the surface of a metastasized colorectal cancer cell in the individual is increased by administering to the individual an amount of an ST receptor ligand sufficient to result in an increase in the number of ST receptor protein molecules on the surface of the cell. The ST receptor ligand is administered to the individual in such a manner to provide a sufficient number of ST receptor ligand molecules to come into contact with ST receptor proteins on the surface of the metastasized colorectal cancer cell in the individual for a sufficient time to result in an increase in the number of ST receptor protein molecules on the surface of the cell.

The present invention relates to methods of imaging a metastasized colorectal tumor in an individual who has metastasized colorectal cancer. The methods comprise the steps of increasing the number of ST receptor molecules on the surface of a metastasized colorectal cancer cell in the individual and then administering an pharmaceutical imaging composition that comprises components which target ST receptor for delivery of an imaging agent. The number of ST receptor molecules on the surface of a metastasized colorectal cancer cell in the individual is increased by administering to the individual an amount of an ST receptor ligand sufficient to result in an increase in the number of ST receptor protein molecules on the surface of the cell. The ST receptor ligand is administered to the individual in such a manner to provide a sufficient number of ST receptor ligand molecules to come into contact with ST receptor proteins on the surface of the metastasized colorectal cancer cell in the individual for a sufficient time to result in an increase in the number of ST receptor protein molecules on the surface of the cell.

The present invention relates to methods of determining whether an individual has metastasized colorectal cancer. The methods comprise the steps of increasing the number of ST receptor molecules on the surface of a metastasized colorectal cancer cell in the individual, obtaining a sample of extraintestinal body fluid and/or tissue from the individual, and detecting the presence of mRNA encoding ST receptor in the sample. The presence of the mRNA indicates that the individual has metastatic colorectal cancer. The number of ST receptor molecules on the surface of a metastasized colorectal cancer cell in the individual is increased by administering to the individual an amount of an ST receptor ligand sufficient to result in an increase in the number of ST receptor protein molecules on the surface of the cell. The ST receptor ligand is administered to the individual in such a manner to provide a sufficient number of ST receptor ligand molecules to come into contact with ST receptor proteins on the surface of the metastasized colorectal cancer cell in the individual for a sufficient time to result in an increase in the number of ST receptor protein molecules on the surface of the cell.

The present invention relates to methods of delivering an active compound to a colorectal cell in an individual. The methods comprise the steps of increasing the number of ST receptor molecules on the surface of a colorectal cell in the individual. The number of ST receptor molecules on the surface of a colorectal cell in the individual is increased by administering to the individual an amount of an ST receptor ligand sufficient to result in an increase in the number of ST receptor protein molecules on the surface of the cell. The ST receptor ligand is administered to the individual in such a manner to provide a sufficient number of ST receptor ligand molecules to come into contact with ST receptor proteins on the surface of the colorectal cell in the individual for a sufficient time to result in an increase in the number of ST receptor protein molecules on the surface of the cell.

The present invention relates to methods of therapeutically vaccinating an individual who has metastasized colorectal cancer, i.e. inducing an immune response against metastatic colorectal tumor cells. The methods comprise the steps of increasing the number of ST receptor molecules on the surface of a metastasized colorectal cancer cell in the individual. The number of ST receptor molecules on the surface of a metastasized colorectal cancer cell in the individual is increased by administering to the individual an amount of an ST receptor ligand sufficient to result in an increase in the number of ST receptor protein molecules on the surface of the cell. The ST receptor ligand is administered to the individual in such a manner to provide a sufficient number of ST receptor ligand molecules to come into contact with ST receptor proteins on the surface of the metastasized colorectal cancer cell in the individual for a sufficient time to result in an increase in the number of ST receptor protein molecules on the surface of the cell.

The present invention relates to methods of treating an individual who has primary colorectal, gastric or esophageal cancer comprising the step of administering to the individual an effective amount of ST receptor binding agent for an effective amount of time to inhibit metastasis of human primary colorectal, gastric or esophageal cancer cells. The ST receptor ligand is administered to the individual in such a manner as to provide a sufficient number of ST receptor ligand molecules to come into contact with ST receptor proteins on the surface of primary colorectal, gastric or esophageal cancer cells in the individual for a sufficient time to result in an inhibition of metastasis.

The present invention relates to methods of treating an individual who has metastatic colorectal, gastric or esophageal cancer comprising the step of administering to the individual an effective amount of ST receptor binding agent for an effective amount of time to inhibit metastasis of human primary colorectal, gastric or esophageal cancer cells. The ST receptor ligand is administered to the individual in such a manner as to provide a sufficient number of ST receptor ligand molecules to come into contact with ST receptor proteins on the surface of metastatic colorectal, gastric or esophageal cancer cells in the individual for a sufficient time to result in an inhibition of metastasis.

The present invention further relates to pharmaceutical compositions, including injectable pharmaceutical compositions, that comprise an amount of an ST receptor ligand sufficient to inhibit metastasis of human primary colorectal, gastric and esophageal cancer in an individual who has primary colorectal, gastric and esophageal cancer.

The present invention further relates to pharmaceutical compositions, including injectable pharmaceutical compositions, that comprise an amount of an ST receptor ligand sufficient to inhibit further metastasis of human metastatic colorectal, gastric and esophageal cancer in an individual who has metastatic colorectal, gastric and esophageal cancer.

The present invention relates to methods of preventing colorectal, gastric or esophageal cancer an individual who has colorectal polyps or precancerous lesions in the stomach or esophagus comprising the step of administering to the individual an effective amount of ST receptor binding agent for an effective amount of time to inhibit cells of the colorectal polyps or precancerous lesions in the stomach or esophagus to transform into cancer cells. The ST receptor ligand is administered to the individual in such a manner as to provide a sufficient number of ST receptor ligand molecules to come into contact with ST receptor proteins on the surface of cells of the colorectal polyps or precancerous lesions in the stomach or esophagus in the individual for a sufficient time to result in an inhibit transformation of the cells into cancer cells.

The present invention further relates to pharmaceutical compositions, including injectable pharmaceutical compositions, that comprise an amount of an ST receptor ligand sufficient to inhibit transformation of cells of colorectal polyps or precancerous lesions in the stomach or esophagus in colorectal, gastric and esophageal cancer cells in an individual.

The present invention relates to methods of treating an individual who has primary and/or metastasic human colorectal, gastric or esophageal cancer. According to the present invention, the methods comprise administering to such an individual, an effective amount of ST receptor binding agent in combination with an effective amount calcium to inhibit cell proliferation and metastasis.

The present invention further relates to pharmaceutical compositions, including injectable pharmaceutical compositions, that comprise an ST receptor ligand in combination with Calcium in an amount effective to inhibit cell proliferation and metastasis in an individual with colorectal, gastric or esophageal in cancer.

The present invention relates to methods of treating an individual who has polyps in the colon or precancerous lesions in the stomach or esophagus. According to the present invention, the methods comprise administering to such an individual, an ST receptor binding agent in combination with Calcium in an amount effective to inhibit transformation of the cells of colorectal polyps or precancerous lesions in the stomach or esophagus into cancer cells.

The present invention further relates to pharmaceutical compositions, including injectable pharmaceutical compositions, that comprise an ST receptor ligand, and Calcium in an amount sufficient to inhibit transformation of cells of colorectal polyps or precancerous lesions in the stomach or esophagus into colorectal, gastric and esophageal cancer cells in an individual.

BRIEF DESCRIPTION OF THE FIGURES

FIGS. 1a-1d illustrate the geographic imbalance between colorectal cancer and infections with ETEC which produce enterotoxins that suppress human colon carcinoma cell proliferation. FIG. 1a shows worldwide geographic distribution of ST-producing ETEC infections and the incidence of colorectal cancer. The risk of infection with ST-producing ETEC was estimated from the risk of travelers' diarrhea. The incidence of colorectal cancer is represented as the age-adjusted rate using the World Standard Population (ASR-W) and is expressed per 100,000. Linear regression analysis was generated to fit the mean values for each risk category. FIG. 1b shows data indicating ST (1 µM) inhibits DNA synthesis in colon cancer cells expressing GC-C [T84 cells; P<0.01 for control vs. Student's t test (ST)] but not in those cells that do not express GC-C (SW480 cells). Tumor cell proliferation, % (y axis) is defined as the amount of DNA synthesis in treated cells as a percentage of the amount of DNA synthesis in parallel control cultures. FIG. 1c shows data indicating that in T84 cells, the antiproliferative effects of ST correlate with [cGMP]i but not intracellular cAMP accumulation. FIG. 1d shows that inhibitors of downstream effectors of cGMP, including PKG (1 µM KT5823, 50 µM RP8pCPT-cGMP), cAMP-dependent protein kinase (0.5 µM KT5720, 50 µM RP-cAMPs), and cGMP-regulated phosphodiesterase 3 [10 µM milrinone (MRL)], did not alter the inhibition of proliferation induced by ST. In contrast, an inhibitor of CNG channels, L-DLT (200 µM), blocked the effect of ST on proliferation (P>0.1 for control vs. L-DLT, Student's t test). The concentrations of inhibitors used are those that selectively and completely inhibit their target enzymes: PKG-I and -II (KT5823: Ki=234 nM; RP8pCPT-cGMP: Ki=500 nM; refs. 20, 48, and 49), cAMP-dependent protein kinase I and II (KT5720: Ki=56 nM; RP-cAMPs: Ki=10 µM; refs. 50 and 51), and phosphodiesterase 3 (milrinone: Ki=300 nM; ref. 52). The concentration of L-DLT used abolished ST-induced 45 Ca2+ influx in the rat colon (40). Data are the mean±SEM of a representative experiment performed in triplicate.

FIGS. 2a-2f show ST induces an L-DLT-sensitive current in human colon carcinoma cells. FIG. 2a shows data from a time-course of steady-state outward current recorded at the end of 200- ms-long depolarizing rectangular pulses from a holding potential of −40 mV to +30 mV. The period of drug application is indicated by corresponding horizontal bars above the data plot. (Top) Original current traces corresponding to specific points along the time course under control conditions (1), following application of 500 nM ST (2), and in the combined presence of ST plus 200 µM L-DLT (3). FIG. 2b shows that average current at +30 mV under control conditions, in the presence of ST, and in the presence of ST plus L-DLT (n=6, mean±SEM). FIG. 2c shows voltage-current relationships obtained at the holding potential of −40 mV in response to 1-s-long ramp pulses from −120 mV to +110 mV under control conditions, in the presence of ST, and in the presence of ST plus L-DLT. ST induced a significant shift of the reversal potential (ΔEm=−27.5±2.6 mV, n=6, mean±SEM) that was reversed by L-DLT.

FIG. 3a shows that [cGMP]i was increased by application of the membrane-permeable analog, 8-br-cGMP (2.5. mM), which, in a time-dependent manner, activated a membrane current sensitive to 200 µM L-DLT. (Right) Original current traces recorded in response to 200-ms depolarizing rectangular pulses from a holding potential of −40 mV to +30 mV correspond to points along the time course under control conditions (1), in the presence of 8-br-cGMP (2), and in the combined presence of 8-br-cGMP plus L-DLT (3). FIG. 3b shows voltage-current relationships obtained at the holding potential of −40 mV in response to 1-s-long ramp pulses from −100 mV to +110 mV under control conditions and in the presence of 8-br-cGMP. FIG. 3c shows average current at +30 mV in the presence of 8-br-cGMP and in the presence of 8-br-cGMP plus L-DLT (n=4, mean±SEM). FIG. 3d shows inhibition of cell proliferation by 8-br-cGMP (5 mM) was blocked by 200 µM L-DLT. Data are the mean±SEM of a representative experiment performed in triplicate.

FIGS. 4a and 4b show currents induced by ST (4a) and 8-br-cGMP (4b) are reversed in calcium-free solution. Steady-state outward current recorded at the end of 200-ms-long depolarizing rectangular pulses from a holding potential of −40 mV to +10 mV. FIG. 4c shows average effect of ST (white bars) and 8-br-cGMP (gray bars) in the presence (control; 1.8 mM CaCl2) and absence (Ca-free) of [Ca2+]ext, as well as in the presence of 100 nM charybdotoxin, a specific inhibitor of Kca channels (CTX in the presence of 1.8 mM CaCl2). Data are the mean±SEM of five separate experiments. (Inset) A representative current-voltage relationship defining the effect of charybdotoxin on ST-induced current obtained in response to 0.25 V/s ramped membrane depolarization. FIG. 4d shows ST (1 µM, 20 min) or 8-br-cGMP (5 mM, 40 min) induced influx of 45Ca2+ into colon cancer cells, which was abolished by pretreatment (30 min) with 250 µM L-DLT. Results are expressed as percent increase over respective controls and are the mean±SEM of six (ST) or five (8-br-cGMP) experiments performed in duplicate. FIG. 4e shows ST inhibits cell proliferation, an effect abolished by the cytosolic calcium chelator BAPTA-AM (BAPTA, 20 µM). Dantrolene (DTR, 50 µM), which blocks Ca2+ mobilization from the endoplasmic reticulum, and phenamil (PHE, 1 µM), which blocks Na+/Ca2+ exchange as well as CTX (100 nM), did not reverse ST-mediated inhibition of proliferation. Ionomycin (INM, 1 µM), a calcium ionophore, mimicked on its own the effects of ST (1 µM). Results are expressed as percentage of respective controls and are the mean±SEM of a representative experiment performed in triplicate. FIG. 4f shows ST inhibition of cell proliferation (left scale) depended on [Ca2+]ext, with an EC50 estimated at 127 µM. The inability of ST to inhibit proliferation in the absence of [Ca2+]ext did not reflect failure of ST to bind to GC-C, because induction of [cGMP]i accumulation (right scale) by ST was independent of [Ca2+]ext. Data are the mean±SEM of a representative experiment performed in triplicate.

DESCRIPTIONS OF PREFERRED EMBODIMENTS OF THE INVENTION

Figure 3A:
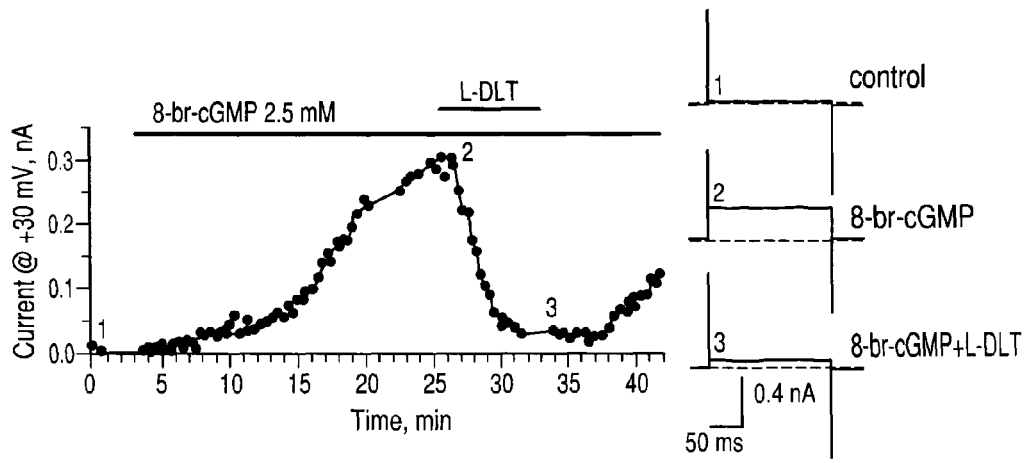
FIGS. 3a-3d show that 8-Br-cGMP induces an L-DLT-sensitive current in, and inhibits proliferation of, human colon carcinoma cells.

As used herein, the terms "ST" and "native ST" are used interchangeably and are meant to refer to heat-stable toxin (ST) which is a peptide produced by *E. coli*, as well as other organisms. STs are naturally occurring peptides which 1) are naturally produced by organisms, 2) which bind to the ST receptor and 3) which activate the signal cascade that mediates ST-induced diarrhea.

As used herein, the terms "ST receptor", "guanylyl cyclase C" and "gcC" are meant to refer to the receptors found on colorectal cells, including local and metastasized colorectal cancer cells, as well as primary and metastatic gastric and esophageal cancer cells, which bind to ST. In normal individuals, ST receptors are found exclusively in cells of intestine, in particular in cells in the duodenum, small intestine (jejunum and ileum), the large intestine, colon (cecum, ascending colon, transverse colon, descending colon and sigmoid colon) and rectum. The nucleotide sequence of cDNA that encodes the human ST receptor protein and the protein sequence are reported in de Sauvage F. J. et al. (Sep. 25, 1991) *Journal of Biological Chemistry* 266(27):17912-8, which is incorporated herein by reference.

As used herein, the term "ST receptor ligand" is meant to refer to compounds which specifically bind to the ST receptor. STs are ST receptor ligands. Other ST receptor ligands include, but are not limited to, guanylin and uroguanylin. An ST receptor ligand may be a peptide or a non-peptide. ST receptor ligands may be conjugated or unconjugated.

As used herein, the term "ST receptor binding peptide" is meant to refer to ST receptor ligands that are peptides. STs are ST receptor binding peptides. Guanylin and uroguanylin are homologous ST receptor binding peptides.

As used herein, the term "ST peptides" is meant to refer to ST receptor binding peptides selected from the group consisting of SEQ ID NO:2, SEQ ID NO:3, SEQ ID NOS:5-56 and fragments and derivatives thereof.

As used herein, the term "fragment" is meant to refer to peptide a) which has an amino acid sequence identical to a portion of an ST receptor binding peptide and b) which is capable of binding to the ST receptor.

As used herein, the term "derivative" is meant to refer to a peptide a) which has an amino acid sequence substantially identical to at least a portion of an ST receptor binding peptide and b) which is capable of binding to the ST receptor.

As used herein, the term "substantially identical" is meant to refer to an amino acid sequence that is the same as the amino acid sequence of an ST peptide except some of the residues are deleted or substituted with conservative amino acids or additional amino acids are inserted.

As used herein, the term "homologous ST receptor peptide" is meant to refer to peptides, other than ST, that bind to the ST receptor.

As used herein, the term "active agent" is meant to refer to compounds that are therapeutic agents or imaging agents.

As used herein, the term "radiostable" is meant to refer to compounds which do not undergo radioactive decay; i.e. compounds which are not radioactive.

As used herein, the term "therapeutic agent" is meant to refer to chemotherapeutics, toxins, radiotherapeutics, targeting agents or radiosensitizing agents.

As used herein, the term "chemotherapeutic" is meant to refer to compounds that, when contacted with and/or incorporated into a cell, produce an effect on the cell including causing the death of the cell, inhibiting cell division or inducing differentiation.

As used herein, the term "toxin" is meant to refer to compounds that, when contacted with and/or incorporated into a cell, produce the death of the cell.

As used herein, the term "radiotherapeutic" is meant to refer to radionuclides which when contacted with and/or incorporated into a cell, produce the death of the cell.

As used herein, the term "targeting agent" is meant to refer compounds which can be bound by and or react with other compounds. Targeting agents may be used to deliver chemotherapeutics, toxins, enzymes, radiotherapeutics, antibodies or imaging agents to cells that have targeting agents associated with them and/or to convert or otherwise transform or enhance co-administered active agents. A targeting agent may include a moiety that constitutes a first agent that is localized to the cell which when contacted with a second agent either is converted to a third agent which has a desired activity or causes the conversion of the second agent into an agent with a desired activity. The result is the localized agent facilitates exposure of an agent with a desired activity to the metastasized cell.

As used herein, the term "radiosensitizing agent" is meant to refer to agents which increase the susceptibility of cells to the damaging effects of ionizing radiation. A radiosensitizing agent permits lower doses of radiation to be administered and still provide a therapeutically effective dose.

As used herein, the term "imaging agent" is meant to refer to compounds whose localization can be detected in vivo.

As used herein, the term "ST receptor binding moiety" is meant to refer to the portion of a compound that constitutes an ST receptor ligand.

As used herein, the term "active moiety" is meant to refer to the portion of a compound that constitutes an active agent.

As used herein, the terms "conjugated compound" and "conjugated composition" are used interchangeably and meant to refer to a compound which comprises an ST receptor binding moiety and an active moiety and which is capable of binding to the ST receptor. Conjugated compounds according to the present invention comprise a portion which constitutes an ST receptor ligand and a portion which constitutes an active agent. Thus, conjugated compounds according to the present invention are capable of specifically binding to the ST receptor and include a portion which is a therapeutic agent or imaging agent. Conjugated compositions may comprise crosslinkers and/or molecules that serve as spacers between the moieties.

As used herein, the term "non-colorectal sample" and "extra-intestinal sample" are used interchangeably and meant to refer to a sample of tissue or body fluid from a source other than colorectal tissue. In some preferred embodiments, the non-colorectal sample is a sample of tissue such as lymph nodes. In some preferred embodiments, the non-colorectal sample is a sample of extra-intestinal tissue which is an adenocarcinoma of unconfirmed origin. In some preferred embodiments, the non-colorectal sample is a blood sample.

As used herein, the term "colorectal cancer" is meant to include the well-accepted medical definition that defines colorectal cancer as a medical condition characterized by cancer of cells of the intestinal tract below the small intestine (i.e. the large intestine (colon), including the cecum, ascending colon, transverse colon, descending colon, and sigmoid colon, and rectum). Additionally, as used herein, the term "colorectal cancer" is meant to further include medical conditions which are characterized by cancer of cells of the duodenum and small intestine (jejunum and ileum). The definition of colorectal cancer used herein is more expansive than the common medical definition but is provided as such since the cells of the duodenum and small intestine also contain ST receptors and are therefore amenable to the methods of the present invention using the compounds of the present invention.

As used herein, the term "gastric cancer" is meant to include the well-accepted medical definition that defines "gastric cancer" as a medical condition characterized by cancer of cells of the gastric cavity as defined by the esophogastric junction to the pyloric sphincter. The term as used herein is also meant to refer to the various forms of cancer of the stomach and esophagus and may include some poorly defined precancerous conditions, such as, for example, Barrett's esophagus and GERD.

As used herein, the term "esophageal cancer" is meant to include the well-accepted medical definition that defines "esophageal cancer" as a medical condition characterized by cancer of cells of the esophagus as defined by the oral cavity, esophagus and including the esophogastric junction. The term as used herein is also meant to refer to the various forms of cancer of the stomach and esophagus and may include some poorly defined precancerous conditions, such as, for example, Barrett's esophagus and GERD.

As used herein, the term "primary" tumor cell is meant to refer to cancer cells which are not metastatic in character and are located in the specific tissue or organ in which the cancer originated. The present invention relates to methods of delivering active agents to primary gastric and esophageal cancer cells.

As used herein, the term "metastasis" or "metastatic" is meant to refer to the process in which cancer cells originating in one organ or part of the body relocate to another part of the body and continue to replicate. Metastasized cells subsequently form tumors which may further metastasize. Metastasis thus refers to the spread of cancer from the part of the body where it originally occurs to other parts of the body. The present invention relates to methods of delivering active agents to metastasized colorectal, gastric and esophageal cancer cells.

As used herein, the terms "the presence of mRNA encoding ST receptor in a non-colorectal or an extra-intestinal sample" and "the presence of mRNA encoding ST receptor in said sample" are meant to refer to mRNA levels above those observed due to illegitimate transcription. Illegitimate transcription is responsible for background levels of ST receptor expression in non-colorectal cells.

It has been discovered that the proliferation of colorectal, gastric and esophageal cancer cells can be inhibited by contacting the cell with an ST receptor ligand that binds to ST receptors on the cell surface, i.e. an ST receptor ligand. It is known that the cell cycle effect of ST on colorectal, esophageal and gastric cancer cells is instantaneous and that the cells take a complete cell cycle to recover. It also has been shown that the binding of an ST receptor ligand to an ST receptor protein stimulates the accumulation of intracellular concentrations of cGMP. The cytostatic effect of cGMP induced by ST receptor ligands, inhibits the proliferation of human colorectal, gastric and esophageal cancer cells. It has also been discovered that the cytostatic effect of the cGMP accumulation is not mediated by specific cyclic nucleotide-dependent kinases, but, rather a novel molecular mechanism, not previously defined.

There are several applications for methods of inhibiting the proliferation of cancer cells of colorectal, gastric or esophageal origin. For example, cells outside the intestinal tract that express ST receptors are metastasized colorectal cancer cells or primary or metastatic gastric or esophageal cancer cells. The ST receptors are targets for in vivo delivery of ST receptor binding ligand to inhibit the proliferation of colorectal, gastric and esophageal cancer cells. The discovery of a means to inhibit the proliferation of such cancer cells by contacting the ST receptor with an effective amount of ST receptor binding protein is useful in conjunction with known therapeutic methods to enhance the effectiveness of such methods. Accordingly, the present invention provides for improved in vivo therapeutic methods comprising the steps of first inhibiting the proliferation of metastatic colorectal and primary and metastatic gastric and esophageal cancer cells and then treating with a therapeutic agent. The present invention also provides therapeutic methods for treating primary colorectal cancer.

In addition, it has been discovered that metastasis of primary colorectal, gastric and esophageal cancer cells as well as further metastasis of metastasized colorectal, gastric and esophageal cancer cells can be inhibited by contacting the cell with an ST receptor ligand that binds to ST receptors on the cell surface, i.e. an ST receptor ligand. There are several applications for methods of inhibiting metastasis of colorectal, gastric or esophageal cancer cells. For example, administration of an amount of ST receptor ligand effective to inhibit metastasis can be undertaken upon initial diagnosis of primary cancer. The administration can be directed at the site of the primary cancer as well as administered systemically. In some embodiments, the administration of an amount of ST receptor ligand effective to inhibit metastasis is undertaken before during or after surgical removal of the cancer and surrounding tissue. The site of cancer as well as other tissue of the effected organ is contacted directly with ST receptor ligand. If performed during surgery, the organ may be washed with a solution containing the ST receptor ligand. If performed prior to or, post-surgery, the ST receptor ligand is delivered to the organ. Systemic administration also may be performed in newly diganosed patients in order to prevent metastasis arising from any undetected metastasized cancer including micrometastses. The administration of an amount of ST receptor ligand effective to inhibit metastasis may be undertaken upon discovery of metastatic disease including directly at the site of any metastic cancer as well as systemically. The ST receptors are targets for in vivo delivery of ST receptor binding ligand to inhibit the metastasis of colorectal, gastric and esophageal cancer cells. The effective amount of ST receptor binding protein to inhibit metastas may be delivered in conjunction with known therapeutic methods to enhance the effectiveness of such methods. Accordingly, the present invention provides for improved in vivo therapeutic methods comprising the steps of first inhibiting metastasis of primary and metastatic colorectal, gastric and esophageal cancer cells and then treating with a therapeutic agent. The present invention also provides therapeutic methods for treating primary colorectal cancer.

Another embodiment of the invention arises from the discovery that treatment of precancerous polyps and lesions in the colon, stomach or esophagus can prevent such precancerous cells and tissue from becoming transformed into cancer. Accordingly, the present invention provides methods of preventing precancerous polyps and lesions in the colon, stomach or esophagus in an individual from becoming transformed into cancer by administering an amount of ST receptor ligand sufficent to inhibit such transformation. The ST receptor ligand may be administered directly to the polyps or lesions or in some cases administered systemically. In some embodiments, upon detection of precancerous polyps or lesions in an individual, an amount of ST receptor ligand sufficient to inhibit transformation of such polyps or lesions is administered to the individual. In some embodiments, individuals may undergo a preventive course of ST receptor ligand without prior detection of precancerous conditions. In such embodiments, the individual is administered an amount of of ST receptor ligand sufficient to inhibit transformation of such polyps or lesions either by administration of an amount of ST receptor ligand effective to inhibit transformation directly to the esophagus, stomach or colorectal tract or systemically.

The method of inhibiting the proliferation of colorectal, gastric and esophageal cancer cells followed by treatment with known therapeutic agents described above can be followed by another step of imaging in order to determine the extent of the decrease in proliferation of the colorectal, gastric and esophageal cancer cells.

It has been discovered that the number of ST receptors on the cell surface of a cell that expresses ST receptors, i.e. a cell of colorectal origin, can be increased by contacting the cell with a ligand which binds to ST receptors on the cell surface, i.e. an ST receptor ligand. ST receptor protein/ST receptor ligand binding upregulates ST receptor gene expression or otherwise affects the cells to result in an increase in the number of ST receptors on the cell surface of a cell. There are several applications for methods of increasing the number of ST receptors on cells of colorectal origin. For example, cells outside the intestinal tract that express ST receptors are metastasized colorectal cancers and the ST receptors are targets for in vivo delivery of therapeutic and imaging agents to treat and image, respectively, metastatic colorectal cancer. The discovery of a means to upregulate ST receptor expression is useful to enhance the effectiveness of such methods. Accordingly, the present invention provides for improved in vivo therapeutic and imaging/diagnostic methods by increasing the number of targets for therapeutic and imaging agents on metastatic colorectal cancer cells. Similarly, in vitro screening/diagnostic methods which employ the detection of ST receptors or evidence of the expression thereof in extraintestinal samples as a marker for metastatic colorectal cancer. Upregulation of ST receptor expression is useful to improve in vitro diagnostic assays by increasing the amount of marker, protein or nucleic acid, to be detected. In addition, ST receptors are used to target and facilitate delivery of material to cells of colorectal origin including normal cells and cells from primary tumors as well as metastatic disease. Compounds such as gene therapeutics, antisense compounds, therapeutic proteins and pharmacologically active compounds conjugated to ST receptor ligands are targeted to and taken up by cells expressing ST receptors. In applications where ST receptors are targeted for delivery of compounds to cells, such as, for example, the delivery of therapeutic or imaging agents to metastasized colorectal cancer cells or the delivery of therapeutic or prophylactic compounds such as, for example, genetic material to normal colon cells or primary colon cancer tumors, increasing the number of ST receptors on the surface of the cell increases the delivery of the compounds to the cell.

High specificity of binding of ST receptor ligand to ST receptors is desired for better delivery of compounds. Specificity has been found to be directly correlated to the number of binding-site receptors on the subject cell. The only theoretical limitation to the utilization of targeting imaging and therapeutic agents to ST receptors is the number of ST receptors on the colorectal cells. The present invention has the potential of increasing the number of guanylyl cyclase C molecules on the surface of colorectal cancer cells 5- to 10-fold. The occurrence of ST receptors on individual colorectal cells occur on the order of $10^4$ to $10^6$ receptors per cell and have an affinity of $10^{-7}$ or better. Metastasized colorectal tumors exhibit similar features.

According to the invention, proliferation in cells that express ST receptors is inhibited using ST receptor ligands, or homologues of ST receptor ligands. In some preferred embodiments, the ST receptor ligand is a homologue of ST receptor binding ligand, such as uroguanylin or guanylin. In other preferred embodiments, the ST receptor ligand is an ST receptor binding peptide. In some preferred embodiments, the ST receptor ligand is an ST receptor peptide selected from the group consisting of: SEQ ID NO:2, SEQ ID NO:3, SEQ ID NOS:5-56 and fragments and derivatives thereof. In some preferred embodiments, the ST receptor ligand is a modified ST receptor binding peptide which is chemically altered to prevent or inhibit degradation in vivo. For example, N terminal capping to prevent or inhibit N terminal peptidases is well known and can be routinely undertaken. In some preferred embodiments, the ST receptor ligand is an anti-ST receptor antibody. In some preferred embodiments, the ST receptor ligand is an anti-ST receptor monoclonal antibody.

According to the invention, ST receptor expression in cells which express ST receptors is increased using ST receptor ligands. In some preferred embodiments, the ST receptor ligand is an ST receptor binding peptide. In some preferred embodiments, the ST receptor ligand is an ST receptor peptide selected from the group consisting of: SEQ ID NO:2, SEQ ID NO:3, SEQ ID NOS:5-56 and fragments and derivatives thereof. In some preferred embodiments, the ST receptor ligand is a modified ST receptor binding peptide which is chemically altered to prevent or inhibit degradation in vivo. For example, N terminal capping to prevent or inhibit N terminal peptidases is well known and can be routinely undertaken. In some preferred embodiments, the ST receptor ligand is an anti-ST receptor antibody. In some preferred embodiments, the ST receptor ligand is an anti-ST receptor monoclonal antibody.

SEQ ID NO:1 discloses a nucleotide sequence which encodes 19 amino acid ST, designated ST Ia, reported by So and McCarthy (1980) *Proc. Natl. Acad. Sci. USA* 77:4011, which is incorporated herein by reference.

The amino acid sequence of ST Ia is disclosed in SEQ ID NO:2.

SEQ ID NO:3 discloses the amino acid sequence of an 18 amino acid peptide which exhibits ST activity, designated ST I*, reported by Chan and Giannella (1981) *J. Biol. Chem.* 256:7744, which is incorporated herein by reference.

SEQ ID NO:4 discloses a nucleotide sequence which encodes 19 amino acid ST, designated ST Ib, reported by Mosely et al. (1983) *Infect. Immun.* 39:1167, which is incorporated herein by reference.

The amino acid sequence of ST Ib is disclosed in SEQ ID NO:5.

A 15 amino acid peptide called guanylin which has about 50% sequence homology to ST has been identified in mammalian intestine (Currie, M. G. et al. (1992) *Proc. Natl. Acad Sci. USA* 89:947-951, which is incorporated herein by reference). Guanylin binds to ST receptors and activates guanylate cyclase at a level of about 10- to 100-fold less than native ST. Guanylin may not exist as a 15 amino acid peptide in the intestine, gastric or esophagus but rather as part of a larger protein in that organ. The amino acid sequence of guanylin from rodent is disclosed as SEQ ID NO:6.

SEQ ID NO:7 is an 18 amino acid fragment of SEQ ID NO:2. SEQ ID NO:8 is a 17 amino acid fragment of SEQ ID NO:2. SEQ ID NO:9 is a 16 amino acid fragment of SEQ ID NO:2. SEQ ID NO:10 is a 15 amino acid fragment of SEQ ID NO:2. SEQ ID NO:11 is a 14 amino acid fragment of SEQ ID NO:2. SEQ ID NO:12 is a 13 amino acid fragment of SEQ ID NO:2. SEQ ID NO:13 is an 18 amino acid fragment of SEQ ID NO:2. SEQ ID NO:14 is a 17 amino acid fragment of SEQ ID NO:2. SEQ ID NO:15 is a 16 amino acid fragment of SEQ ID NO:2. SEQ ID NO:16 is a 15 amino acid fragment of SEQ If NO:2. SEQ ID NO:17 is a 14 amino acid fragment of SEQ ID NO:2.

SEQ ID NO:18 is a 17 amino acid fragment of SEQ ID NO:3. SEQ ID NO:19 is a 16 amino acid fragment of SEQ ID NO:3. SEQ ID NO:20 is a 15 amino acid fragment of SEQ ID NO:3. SEQ ID NO:21 is a 14 amino acid fragment of SEQ ID NO:3. SEQ ID NO:22 is a 13 amino acid fragment of SEQ ID NO:3. SEQ ID NO:23 is a 17 amino acid fragment of SEQ ID NO:3. SEQ ID NO:24 is a 16 amino acid fragment of SEQ ID NO:3. SEQ ID NO:25 is a 15 amino acid fragment of SEQ ID NO:3. SEQ ID NO:26 is a 14 amino acid fragment of SEQ BD NO:3.

SEQ ID NO:27 is an 18 amino acid fragment of SEQ ID NO:5. SEQ ID NO:28 is a 17 amino acid fragment of SEQ ID NO:5. SEQ ID NO:29 is a 16 amino acid fragment of SEQ ID NO:5. SEQ ID NO:30 is a 15 amino acid fragment of SEQ ID NO:5. SEQ ID NO:31 is a 14 amino acid fragment of SEQ ID NO:5. SEQ ID NO:32 is a 13 amino acid fragment of SEQ ID NO:5. SEQ ID NO:33 is an 18 amino acid fragment of SEQ ID NO:5. SEQ ID NO:34 is a 17 amino acid fragment of SEQ ID NO:5. SEQ ID NO:35 is a 16 amino acid fragment of SEQ ID NO:5. SEQ ID NO:36 is a 15 amino acid fragment of SEQ ID NO:5. SEQ ID NO:37 is a 14 amino acid fragment of SEQ ID NO:5.

SEQ ID NO:27, SEQ ID NO:31, SEQ ID NO:36 AND SEQ ID NO:37 are disclosed in Yoshimura, S., et al. (1985) *FEBS Lett.* 181:138, which is incorporated herein by reference.

SEQ ID NO:38, SEQ ID NO:39 and SEQ ID NO:40, which are derivatives of SEQ ID NO:3, are disclosed in Waldman, S. A. and O'Hanley, P. (1989) *Infect. Immun.* 57:2420, which is incorporated herein by reference.

SEQ ID NO:41, SEQ ID NO:42, SEQ ID NO:43, SEQ ID NO:44 and SEQ ID NO:45, which are a derivatives of SEQ ID NO:3, are disclosed in Yoshimura, S., et al. (1985) *FEBS Lett.* 181:138, which is incorporated herein by reference.

SEQ ID NO:46 is a 25 amino acid peptide derived from *Y. enterocolitica* which binds to the ST receptor.

SEQ ID NO:47 is a 16 amino acid peptide derived from *V. cholerae* which binds to the ST receptor. SEQ ID NO:47 is reported in Shimonishi, Y., et al. *FEBS Lett.* 215:165, which is incorporated herein by reference.

SEQ ID NO:48 is an 18 amino acid peptide derived from *Y. enterocolitica* which binds to the ST receptor. SEQ ID NO:48 is reported in Okamoto, K., et al. *Infec. Immun.* 55:2121, which is incorporated herein by reference.

SEQ ID NO:49, is a derivative of SEQ ID NO:5.

SEQ ID NO:50, SEQ ID NO:51, SEQ ID NO:52 and SEQ ID NO:53 are derivatives.

SEQ ID NO:54 is the amino acid sequence of guanylin from human.

SEQ ID NO:55 is the amino acid sequence of uroguanylin from rat. Miyazato, M., et al, FEBS Lett. 398 (2-3), 170-174 (1996); and Blanchard, R. K. and Cousins, R. J., Am. J. Physiol. 272 (5 Pt 1), G972-G978 (1997) which are incorporated herein by reference.

SEQ ID NO:56 is the amino acid sequence of uroguanylin from human. Hill, O., et al, Biochim. Biophys. Acta 1253 (2), 146-149 (1995); Miyazato, M., et al., Biochem. Biophys. Res. Commun. 219 (2), 644-648 (1996); and Miyazato,M., et al., Genomics 43 (3), 359-365 (1997) which are incorporated herein by reference.

In some preferred embodiments, conjugated compounds comprise ST receptor binding moieties that comprise amino acid sequences selected from the group consisting of SEQ ID NO:2, SEQ ID NO:3, SEQ ID NOS:5-56 and fragments and derivatives thereof.

Those having ordinary skill in the art can readily design and produce derivatives having substantially identical amino acid sequences of ST peptides with deletions and/or insertions and/or conservative substitutions of amino acids. For example, following what are referred to as Dayhof's rules for amino acid substitution (Dayhof, M. D. (1978) *Nat. Biomed. Res. Found.*, Washington, D.C. Vol. 5, supp. 3), amino acid residues in a peptide sequence may be substituted with comparable amino acid residues. Such substitutions are well known and are based the upon charge and structural characteristics of each amino acid. Derivatives include fragments of ST receptor binding peptides with deletions and/or insertions and/or conservative substitutions.

In some embodiments, ST receptor binding peptides comprise D amino acids. As used herein, the term "D amino acid peptides" is meant to refer to ST receptor binding peptides, fragments or derivatives which comprise at least one and preferably a plurality of D amino acids which are capable of binding to the ST receptor. The use of D amino acid peptides is desirable as they are less vulnerable to degradation and therefore have a longer half-life.

In some embodiments, ST receptor binding peptides, including D amino acid peptides, are conformationally restricted to present and maintain the proper structural conformation for binding to the ST receptor. The compositions may comprise additional amino acid residues required to achieve proper three dimensional conformation including residues which facilitate circularization or desired folding.

It is preferred that the ST receptor ligand be as small as possible. Thus it is preferred that the ST receptor ligand be a non-peptide small molecule or small peptide, preferably less than 25 amino acids, more preferably less than 20 amino acids. In some embodiments, the ST receptor ligand is less than 15 amino acids. ST receptor binding peptides comprising less than 10 amino acids and ST receptor binding peptides less than 5 amino acids may also be used. It is within the scope of the present invention to include larger molecules which serve as ST receptor binding moieties including, but not limited to molecules such as antibodies, fragments of antibodies, FAbs and F(Ab)$_2$s which specifically bind to ST receptor.

ST may be isolated from natural sources using standard techniques. Additionally, ST receptor binding peptides and conjugated compositions or portions thereof which are peptides may be prepared routinely by any of the following known techniques.

Antibodies include polyclonal and monoclonal antibodies as well as Fab fragments, F(ab)$_2$ fragments and other modifications and products of antibody engineering. Humanized, primatized and modified forms of antibodies to render them less immunogenic are antibodies according to the invention and may be used in the methods of the invention. Antibodies which specifically recognize ST receptor protein have been generated previously and are reported in Vaandrager et al., 1993 *J. Biolog. Chem.* 268:2174, which is incorporated herein by reference. Those having ordinary skill in the art can produce monoclonal antibodies which specifically bind to ST receptor using standard techniques and readily available starting materials. The techniques for producing monoclonal antibodies are outlined in Harlow, E. and D. Lane, (1988) *ANTIBODIES: A Laboratory Manual*, Cold Spring Harbor Laboratory, Cold Spring Harbor N.Y., which is incorporated herein by reference, provide detailed guidance for the production of hybridomas and monoclonal antibodies which specifically bind to target proteins. Briefly, the ST receptor molecule or a molecule which includes an epitope that is immunogenically cross reactive to ST receptor is injected into mice. The spleen of the mouse is removed, the spleen cells are isolated and fused with immortalized mouse cells. The hybrid cells, or hybridomas, are cultured and those cells which secrete antibodies are selected. The antibodies are analyzed and, if found to specifically bind to the protein of interest, the hybridoma which produces them is cultured to produce a continuous supply of antigen specific antibodies. Techniques for engineering antibodies are described in U.S. Pat. Nos. 5,530,101, 5,585,089, and 5,225,539, Winter and Millstein (1991) Nature 349:293, and Larrich and Fry (1991) Hum. Antibod. and Hybridomas 2:17, which are each incorporated herein by reference.

ST receptor binding ligands may be identified by routine screening technology to identify compounds that bind to ST receptor. It is preferred that such compounds bind to ST receptor with an affinity of greater than about that of lymphoguanylin (SEQ ID NO:54) and more preferably that of *E. coli* heat stable enterotoxin (SEQ ID NO:2).

Technology is widely available for screening libraries of compounds including peptides and non-peptides to identify those that bind to proteins such as Brenner, S. and R. A. Lerner, Proc. Natl. Acad. Sci. USA 89:5381-5383 (June 1992); Cull, M. G. et al., Proc. Natl. Acad. Sci. USA 89:1865-1869 (March 1992); and Fodor, S. P. A. et al. Science 251: 767-773 (Feb. 15, 1991), which are each incorporated herein by reference. The following patents, which are each incorporated herein by reference, describe methods of making random peptide or non-peptide libraries and screening such libraries to identify compounds that bind to target proteins. As used in the present invention, ST receptors can be the targets used to identify the peptide and non-peptide ST receptor ligands generated and screened as disclosed in the patents. U.S. Pat. No. 5,270,170 issued to Schatz et al. on Dec. 14, 1993, and U.S. Pat. No. 5,338,665 issued to Schatz et al. on Aug. 16, 1994, which are both incorporated herein by reference, refer to peptide libraries and screening methods which can be used to identify ST receptor ligands according to the invention. U.S. Pat. No. 5,395,750 issued to Dillon et al. on Mar. 7, 1995, which is incorporated herein by reference, refers to methods of producing proteins which bind to predetermined antigens. Such methods can be used to produce ST receptor ligands according to the invention. U.S. Pat. No. 5,223,409 issued to Ladner et al. on Jun. 29, 1993, which is incorporated herein by reference, refers to the directed evolution to novel binding proteins. Such proteins may be produced and screened as disclosed therein to identify ST receptor ligands according to the invention. U.S. Pat. No. 5,366,862 issued to Venton et al. on Nov. 22, 1994, which is incorporated herein by reference, refers to methods for generating and screening useful peptides. The methods herein described can be used to identify ST receptor ligands according to the invention. U.S. Pat. No. 5,340,474 issued to Kauvar on Aug. 23, 1994 as well as U.S. Pat. Nos. 5,133,866, 4,963, 263 and 5,217,869, which are each incorporated herein by reference, can be used to identify ST receptor ligands according to the invention. U.S. Pat. No. 5,405,783 issued to Pirrung et al. on Apr. 11, 1995, which is incorporated herein by reference, refers to large scale photolithographic solid phase synthesis of an array of polymers. The teachings therein can be used to identify ST receptor ligands according to the invention. U.S. Pat. No. 5,143,854 issued to Pirrung et al. on Sep. 1, 1992, which is incorporated herein by reference, refers to a large scale photolithographic solid phase synthesis of polypeptides and receptor binding screening thereof. U.S. Pat. No. 5,384,261 issued to Winkler et al. on Jan. 24, 1995, which is incorporated herein by reference, refers to very large scale immobilized polymer synthesis using mechanically directed flow patterns. Such methods are useful to identify ST receptor ligands according to the invention. U.S. Pat. No. 5,221,736 issued to Coolidge et al. on Jun. 22, 1993, which is incorporated herein by reference, refers to sequential peptide and oligonucleotide synthesis using immunoaffinity techniques. Such techniques may be used to identify ST receptor ligands according to the invention. U.S. Pat. No. 5,412,087 issued to McGall et al. on May 2, 1995, which is incorporated herein by reference, refers to spatially addressable immobilization of oligonucleotides and other biological polymers on surfaces. Such methods may be used to identify ST receptor ligands according to the invention. U.S. Pat. No. 5,324,483 issued to Cody et al. on Jun. 28, 1994, which is incorporated herein by reference, refers to apparatus for multiple simultaneous synthesis. The apparatus and method disclosed therein may be used to produce multiple compounds which can be screened to identify ST receptor ligands according to the invention. U.S. Pat. No. 5,252,743 issued to Barrett et al. on Oct. 12, 1993, which is incorporated herein by reference, refers to spatially addressable immobilization of anti-ligands on surfaces. The methods and compositions described therein may be used to identify ST receptor ligands according to the invention. U.S. Pat. No. 5,424,186 issued to Foder et al. on Jun. 13, 1995, which is incorporated herein by reference, refers to a very large scale immobilized polymer synthesis. The method of synthesizing oligonucleotides described therein may be used to identify ST receptor ligands according to the invention. U.S. Pat. No. 5,420,328 issued to Campbell on May 30, 1995, which is incorporated herein by reference, refers to methods of synthesis of phosphonate esters. The phosphonate esters so produced may be screened to identify compounds which are ST receptor ligands. U.S. Pat. No. 5,288,514 issued to Ellman on Feb. 22, 1994, which is incorporated herein by reference, refers to solid phase and combinatorial synthesis of benzodiazepine compounds on a solid support. Such methods and compounds may be used to identify ST receptor ligands according to the invention.

An assay may be used to test both peptide and non-peptide compositions to determine whether or not they are ST receptor ligands or, to test conjugated compositions to determine if they possess ST receptor binding activity. Such compositions that specifically bind to ST receptors can be identified by a competitive binding assay. The competitive binding assay is a standard technique in pharmacology which can be readily performed by those having ordinary skill in the art using readily available starting materials. Competitive binding assays have been shown to be effective for identifying compositions that specifically bind to ST receptors. Briefly, the assay consists of incubating a preparation of ST receptors (e.g. intestinal membranes from rat intestine, human intestine, T84 cells) with a constant concentration ($1 \times 10^{-10}$M to $5 \times 10^{-10}$M) of $^{125}$I-ST (any ST receptor ligand such as native STs SEQ ID NO:2, SEQ ID NO:3 or SEQ ID NO:5 may be used) and a known concentration of a test compound. As a control, a duplicate preparation of ST receptors are incubated with a duplicate concentration of $^{125}$I-ST in the absence of test compound. Assays are incubated to equilibrium (2 hours) and the amount of $^{125}$I-ST bound to receptors is quantified by standard techniques. The ability of the test compound to bind to receptors is measured as its ability to prevent (compete with) the $^{125}$I-ST from binding. Thus, in assays containing the test compound which bind to the receptor, there will be less radioactivity associated with the receptors. This assay, which is appropriate for determining the ability of any molecule to bind to ST receptors, is a standard competitive binding assay which can be readily employed by those having ordinary skill in the art using readily available starting materials.

ST receptor binding peptides and conjugated compositions or portions thereof which are peptides may be prepared using the solid-phase synthetic technique initially described by Merrifield, in *J. Am. Chem. Soc.*, 15:2149-2154 (1963). Other peptide synthesis techniques may be found, for example, in M. Bodanszky et al., (1976) *Peptide Synthesis*, John Wiley & Sons, 2d Ed.; Kent and Clark-Lewis in *Synthetic Peptides in Biology and Medicine*, p. 295-358, eds. Alitalo, K., et al. Science Publishers, (Amsterdam, 1985); as well as other reference works known to those skilled in the art. A summary of peptide synthesis techniques may be found in J. Stuart and J. D. Young, *Solid Phase Peptide Synthelia*, Pierce Chemical Company, Rockford, Ill. (1984), which is incorporated herein by reference. The synthesis of peptides by solution methods may also be used, as described in *The Proteins*, Vol. II, 3d Ed., p. 105-237, Neurath, H. et al., Eds., Academic Press, New York, N.Y. (1976). Appropriate protective groups for use in such syntheses will be found in the above texts, as well as in J. F. W. McOmie, *Protective Groups in Organic Chemistry*, Plenum Press, New York, N.Y. (1973), which is incorporated herein by reference. In general, these synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptide of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

ST receptor binding peptides and conjugated compositions or portions thereof which are peptides may also be prepared by recombinant DNA techniques. Provision of a suitable DNA sequence encoding the desired peptide permits the production of the peptide using recombinant techniques now known in the art. The coding sequence can be obtained from natural sources or synthesized or otherwise constructed using widely available starting materials by routine methods. When the coding DNA is prepared synthetically, advantage can be taken of known codon preferences of the intended host where the DNA is to be expressed.

To produce an ST receptor binding peptide which occurs in nature, one having ordinary skill in the art can, using well-known techniques, obtain a DNA molecule encoding the ST receptor binding peptides from the genome of the organism that produces the ST receptor binding peptide and insert that DNA molecule into a commercially available expression vector for use in well-known expression systems.

Likewise, one having ordinary skill in the art can, using well known techniques, combine a DNA molecule that encodes an ST receptor binding peptide, such as SEQ ID NO:1 and SEQ ID NO:4, which can be obtained from the genome of the organism that produces the ST, with DNA that encodes a toxin, another active agent that is a peptide or additionally, any other amino acid sequences desired to be adjacent to the ST receptor binding peptide amino acid sequence in a single peptide and insert that DNA molecule into a commercially available expression vector for use in well-known expression systems.

For example, the commercially available plasmid pSE420 (Invitrogen, San Diego, Calif.) may be used for recombinant production in *E. coli*. The commercially available plasmid pYES2 (Invitrogen, San Diego, Calif.) may be used for production in *S. cerevisiae* strains of yeast. The commercially available MaxBac™ (Invitrogen, San Diego, Calif.) complete baculovirus expression system may be used for production in insect cells. The commercially available plasmid pcDNA I (Invitrogen, San Diego, Calif.) may be used for production in mammalian cells such as Chinese Hamster Ovary cells.

One having ordinary skill in the art may use these or other commercially available expression vectors and systems or produce vectors using well-known methods and readily available starting materials. Expression systems containing the requisite control sequences, such as promoters and polyadenylation signals, and preferably enhancers, are readily available and known in the art for a variety of hosts. See e.g., Sambrook et al., *Molecular Cloning a Laboratory Manual*, Second Ed. Cold Spring Harbor Press (1989). Thus, the desired proteins can be prepared in both prokaryotic and eukaryotic systems, resulting in a spectrum of processed forms of the protein.

The most commonly used prokaryotic system remains *E. coli*, although other systems such as *B. subtilis* and *Pseudomonas* are also useful. Suitable control sequences for prokaryotic systems include both constitutive and inducible promoters including the lac promoter, the trp promoter, hybrid promoters such as tac promoter, the lambda phage P1 promoter. In general, foreign proteins may be produced in these hosts either as fusion or mature proteins. When the desired sequences are produced as mature proteins, the sequence produced may be preceded by a methionine which is not necessarily efficiently removed. Accordingly, the peptides and proteins claimed herein may be preceded by an N-terminal Met when produced in bacteria. Moreover, constructs may be made wherein the coding sequence for the peptide is preceded by an operable signal peptide which results in the secretion of the protein. When produced in prokaryotic hosts in this matter, the signal sequence is removed upon secretion.

A wide variety of eukaryotic hosts are also now available for production of recombinant foreign proteins. As in bacteria, eukaryotic hosts may be transformed with expression systems which produce the desired protein directly, but more commonly signal sequences are provided to effect the secretion of the protein. Eukaryotic systems have the additional advantage that they are able to process introns which may occur in the genomic sequences encoding proteins of higher organisms. Eukaryotic systems also provide a variety of processing mechanisms which result in, for example, glycosylation, carboxy-terminal amidation, oxidation or derivatization of certain amino acid residues, conformational control, and so forth.

Commonly used eukaryotic systems include, but are not limited to, yeast, fungal cells, insect cells, mammalian cells, avian cells, and cells of higher plants. Suitable promoters are available which are compatible and operable for use in each of these host types as well as are termination sequences and enhancers, as e.g. the baculovirus polyhedron promoter. As above, promoters can be either constitutive or inducible. For example, in mammalian systems, the mouse metallothionene promoter can be induced by the addition of heavy metal ions.

The particulars for the construction of expression systems suitable for desired hosts are known to those in the art. For recombinant production of the protein, the DNA encoding it is suitably ligated into the expression vector of choice and then used to transform the compatible host which is then cultured and maintained under conditions wherein expression of the foreign gene takes place. The protein of the present invention thus produced is recovered from the culture, either by lysing the cells or from the culture medium as appropriate and known to those in the art.

One having ordinary skill in the art can, using well-known techniques, isolate the protein that is produced.

In some embodiments the ST receptor ligand is formulated as a injectable pharmaceutical composition suitable for parenteral administration. Accordingly, the ST receptor ligand is a sterile, pyrogen-free preparation that has the structural/physical characteristics required for injectable products; i.e. it meets well known standards recognized by those skilled in the art for purity, pH, isotonicity, sterility, and particulate matter.

In some preferred embodiments, the ST receptor ligand administered orally or rectally and the ST receptor ligand is formulated as pharmaceutical composition suitable for oral or rectal administration. Some embodiments providing ST receptor ligand suitable for oral administration provide ST receptor ligand formulated for sustained release. Some embodiments providing ST receptor ligand suitable for oral administration provide ST receptor ligand formulated by enteric coating to release the active agent in the intestine. Enteric formulations are described in U.S. Pat. Nos. 4,601,896, 4,729,893, 4,849,227, 5,271,961, 5,350,741, and 5,399,347, which are each hereby incorporated herein by reference. Oral and rectal formulation are taught in Remington's Pharmaceutical Sciences, 18th Edition, 1990, Mack Publishing Co., Easton Pa. which is incorporated herein by reference.

Alternative embodiments include sustained release formulations and implant devices which provide continuous delivery of ST receptor ligand. In another embodiment, the ST receptor ligand is administered topically, or for application intratumorally, intrathecally, intraventricularly, intrapleurally, intrabronchially, intracranially, or subcutaneously.

The ST receptor ligand is administered to the individual in an amount effective to inhibit the proliferation of cells that express the ST receptor, such as metastatic colorectal cancer cells and primary and metastatic gastric and esophageal cancer cells. In some preferred embodiments, the cells are metastasized human colorectal cancer cells. In other preferred embodiments, the cells are primary or metastasized gastric cancer cells. In other preferred embodiments, the cells are primary or metastasized esophageal cancer cells.

The ST receptor ligand is administered to the individual by any route that will allow for the delivery of the ligand to cells that express ST receptors. In some preferred embodiments, the ST receptor ligand is administered parenterally. In some preferred embodiments, the ST receptor ligand is administered into the circulatory system of the individual. In some embodiments, the ST receptor ligand is administered intravenously. In some embodiments, the ST receptor ligand is administered into the cerebral spinal fluid. In some embodiments, the ST receptor ligand is administered into the lymph system. In some embodiments, the ST receptor ligand is administered intratumorally. In some preferred embodiments, the ST receptor ligand administered orally, rectally, topically, intratumorally, intrathecally, intraventricularly, intrapleurally, intrabronchially, intracranially, or subcutaneously.

When the ST receptor ligand binds to the ST receptor protein on cells expressing the ST receptor, proliferation of the cells is inhibited. An effective amount of ST receptor ligand must be administered to achieve inhibition of proliferation. Generally, ST receptor ligand must be present at a sufficient level for a sustained amount of time to expose cells that express ST receptors to the ST receptor ligand. Generally, enough ST receptor ligand must be administered initially and/or by continuous administration to maintain the concentration of ST ligand to be greater than about $10^{-10}$M, and preferably about $10^{-9}$M or more. It is preferred that such a concentration be maintained for at least about 6 hours, preferably about for at least about 8 hours, more preferably about for at least about 12 hours, in some embodiments at least 16 hours, in some embodiments at least 20 hours and up to about 24 hours or more. Regardless of whether the compound is an ST receptor ligand or ST receptor ligand conjugate which has additional functions such as cytotoxic activity or detectability, it is important that the dosage and administration be sufficient for the ST receptor binding to occur at a sufficient level for sufficient time to inhibit proliferation or to induce a therapeutic effect. Generally, the plasma concentration of ST receptor greater than about $10^{-10}$M must be maintained for at least about 6 hours. Pharmaceutical compositions according to the invention are therefore provided in dosages sufficient to maintain such plasma concentration. Dosage varies depending upon known factors such as the pharmacodynamic characteristics of the particular agent, and its mode and route of administration; age, health, and weight of the recipient; nature and extent of symptoms, kind of concurrent treatment, frequency of treatment, and the effect desired.

In some embodiments, the ST receptor ligand is initially administered to the individual in a loading dose of at least 0.1 nM per 10 kg. bodyweight of the individual. In some embodiments, the ST receptor ligand is initially administered to the individual in a loading dose of at least 0.25 nM per 10 kg. bodyweight of the individual. In some embodiments, the ST receptor ligand is initially administered to the individual in a loading dose of at least 0.5 nM per 10 kg. bodyweight of the individual. In some embodiments, the ST receptor ligand is initially administered to the individual in a loading dose of at least 0.75 nM per 10 kg. bodyweight of the individual. In some embodiments, the ST receptor ligand is initially administered to the individual in a loading dose of at least 1 nM per 10 kg. bodyweight of the individual. In some embodiments, the ST receptor ligand is initially administered to the individual in a loading dose of at least 1.5 nM per 10 kg. bodyweight of the individual. In some embodiments, the ST receptor ligand is initially administered to the individual in a loading dose of at least 2 nM per 10 kg. bodyweight of the individual. In some embodiments, the ST receptor ligand is initially administered to the individual in a loading dose of at least 2.5 nM per 10 kg. bodyweight of the individual. In some embodiments, the ST receptor ligand is initially administered to the individual in a loading dose of at least 3 nM per 10 kg. bodyweight of the individual. In some embodiments, the ST receptor ligand is initially administered to the individual in a loading dose of at least 4 nM per 10 kg. bodyweight of the individual. In some embodiments, the ST receptor ligand is initially administered to the individual in a loading dose of at least 5 nM per 10 kg. bodyweight of the individual. In some embodiments, the ST receptor ligand is initially administered to the individual in a loading dose of at least 7.5 nM per 10 kg. bodyweight of the individual. In some embodiments, the ST receptor ligand is initially administered to the individual in a loading dose of at least 10 nM per 10 kg. bodyweight of the individual. In some embodiments, the loading dose is 0.1-10 nM of ST receptor ligand per 10 kg. bodyweight of said individual. In some embodiments, the loading dose is 0.1-7.5 nM of ST receptor ligand per 10 kg. bodyweight of said individual. In some embodiments, the loading dose is 0.1-5 nM of ST receptor ligand per 10 kg. bodyweight of said individual. In some embodiments, the loading dose is 0.1-2.5 nM of ST receptor ligand per 10 kg. bodyweight of said individual. In some embodiments, the loading dose is 0.1-1.5 nM of ST receptor ligand per 10 kg. bodyweight of said individual. In some embodiments, the loading dose is 0.1-1.0 nM of ST receptor ligand per 10 kg. bodyweight of said individual. In some embodiments, the loading dose is 0.1-0.5 nM of ST receptor ligand per 10 kg. bodyweight of said individual. In some embodiments, the loading dose is 0.1-0.25 nM of ST receptor ligand per 10 kg. bodyweight of said individual. In some embodiments, the loading dose is 0.25-10 nM of ST receptor ligand per 10 kg. bodyweight of said individual. In some embodiments, the loading dose is 0.25-7.5 nM of ST receptor ligand per 10 kg. bodyweight of said individual. In some embodiments, the loading dose is 0.25-5 nM of ST receptor ligand per 10 kg. bodyweight of said individual. In some embodiments, the loading dose is 0.25-2.5 nM of ST receptor ligand per 10 kg. bodyweight of said individual. In some embodiments, the loading dose is 0.25-1.5 nM of ST receptor ligand per 10 kg. bodyweight of said individual. In some embodiments, the loading dose is 0.25-1.0 nM of ST receptor ligand per 10 kg. bodyweight of said individual. In some embodiments, the loading dose is 0.5-0.75 nM of ST receptor ligand per 10 kg. bodyweight of said individual. In some embodiments, the loading dose is 0.25-0.5 nM of ST receptor ligand per 10 kg. bodyweight of said individual.

In some embodiments, the loading dose is 0.5-10 nM of ST receptor ligand per 10 kg. bodyweight of said individual. In some embodiments, the loading dose is 0.5-7.5 nM of ST receptor ligand per 10 kg. bodyweight of said individual. In some embodiments, the loading dose is 0.5-5 nM of ST receptor ligand per 10 kg. bodyweight of said individual. In some embodiments, the loading dose is 0.5-2.5 nM of ST receptor ligand per 10 kg. bodyweight of said individual. In some embodiments, the loading dose is 0.5-1.5 nM of ST receptor ligand per 10 kg. bodyweight of said individual. In some embodiments, the loading dose is 0.5-1.0 nM of ST receptor ligand per 10 kg. bodyweight of said individual. In some embodiments, the loading dose is 0.5-0.75 nM of ST receptor ligand per 10 kg. bodyweight of said individual.

In some embodiments, the loading dose is 0.75-10 nM of ST receptor ligand per 10 kg. bodyweight of said individual. In some embodiments, the loading dose is 0.75-7.5 nM of ST receptor ligand per 10 kg. bodyweight of said individual. In some embodiments, the loading dose is 0.75-5 nM of ST receptor ligand per 10 kg. bodyweight of said individual. In some embodiments, the loading dose is 0.75-2.5 nM of ST receptor ligand per 10 kg. bodyweight of said individual. In some embodiments, the loading dose is 0.75-1.5 nM of ST receptor ligand per 10 kg. bodyweight of said individual. In some embodiments, the loading dose is 0.75-1.0 nM of ST receptor ligand per 10 kg. bodyweight of said individual. In some embodiments, the loading dose is 1-10 nM of ST receptor ligand per 10 kg. bodyweight of said individual. In some embodiments, the loading dose is 1-7.5 nM of ST receptor ligand per 10 kg. bodyweight of said individual. In some embodiments, the loading dose is 1-5 nM of ST receptor ligand per 10 kg. bodyweight of said individual. In some embodiments, the loading dose is 1-2.5 nM of ST receptor ligand per 10 kg. bodyweight of said individual. In some embodiments, the loading dose is 1-1.5 nM of ST receptor ligand per 10 kg. bodyweight of said individual. In some embodiments, the loading dose is 1.5-10 nM of ST receptor ligand per 10 kg. bodyweight of said individual. In some embodiments, the loading dose is 1.5-7.5 nM of ST receptor ligand per 10 kg. bodyweight of said individual. In some embodiments, the loading dose is 1.5-5 nM of ST receptor ligand per 10 kg. bodyweight of said individual. In some embodiments, the loading dose is 1.5-2.5 nM of ST receptor ligand per 10 kg. bodyweight of said individual. In some embodiments, the loading dose is 2.5-10 nM of ST receptor ligand per 10 kg. bodyweight of said individual. In some embodiments, the loading dose is 2.5-7.5 nM of ST receptor ligand per 10 kg. bodyweight of said individual. In some embodiments, the loading dose is 2.5-5 nM of ST receptor ligand per 10 kg. bodyweight of said individual. In some embodiments, the loading dose is 5-10 nM of ST receptor ligand per 10 kg. bodyweight of said individual. In some embodiments, the loading dose is 5-7.5 nM of ST receptor ligand per 10 kg. bodyweight of said individual.

In some embodiments, the ST receptor ligand is administered to the individual by continuous infusion of at least 0.1 nM per 10 kg. bodyweight of the individual per hour. In some embodiments, the ST receptor ligand is administered to the individual by continuous infusion of at least 0.25 nM per 10 kg. bodyweight of the individual per hour. In some embodiments, the ST receptor ligand is administered to the individual by continuous infusion of at least 0.5 nM per 10 kg. bodyweight of the individual per hour. In some embodiments, the ST receptor ligand is administered to the individual by continuous infusion of at least 0.75 nM per 10 kg. bodyweight of the individual per hour. In some embodiments, the ST receptor ligand is administered to the individual by continuous infusion of at least 1 nM per 10 kg. bodyweight of the individual per hour. In some embodiments, the ST receptor ligand is administered to the individual by continuous infusion of at least 1.5 nM per 10 kg. bodyweight of the individual per hour. In some embodiments, the ST receptor ligand is administered to the individual by continuous infusion of at least 2 nM per 10 kg. bodyweight of the individual per hour. In some embodiments, the ST receptor ligand is administered to the individual by continuous infusion of at least 2.5 nM per 10 kg. bodyweight of the individual per hour. In some embodiments, the ST receptor ligand is administered to the individual by continuous infusion of at least 3 nM per 10 kg. bodyweight of the individual per hour. In some embodiments, the ST receptor ligand is administered to the individual by continuous infusion of at least 4 nM per 10 kg. bodyweight of the individual per hour. In some embodiments, the ST receptor ligand is administered to the individual by continuous infusion of at least 5 nM per 10 kg. bodyweight of the individual per hour. In some embodiments, the ST receptor ligand is administered to the individual by continuous infusion of at least 7.5 nM per 10 kg. bodyweight of the individual per hour. In some embodiments, the ST receptor ligand is administered to the individual by continuous infusion of at least 10 nM per 10 kg. bodyweight of the individual per hour. In some embodiments, the dose infused is 0.1-10 nM of ST receptor ligand per 10 kg. bodyweight of said individual per hour. In some embodiments, the dose infused is 0.1-7.5 nM of ST receptor ligand per 10 kg. bodyweight of said individual per hour. In some embodiments, the dose infused is 0.1-5 nM of ST receptor ligand per 10 kg. bodyweight of said individual per hour. In some embodiments, the dose infused is 0.1-2.5 nM of ST receptor ligand per 10 kg. bodyweight of said individual per hour. In some embodiments, the dose infused is 0.1-1.5 nM of ST receptor ligand per 10 kg. bodyweight of said individual per hour. In some embodiments, the dose infused is 0.1-1.0 nM of ST receptor ligand per 10 kg. bodyweight of said individual per hour. In some embodiments, the dose infused is 0.1-0.5 nM of ST receptor ligand per 10 kg. bodyweight of said individual per hour. In some embodiments, the dose infused is 0.1-0.25 nM of ST receptor ligand per 10 kg. bodyweight of said individual per hour. In some embodiments, the dose infused is 0.25-10 nM of ST receptor ligand per 10 kg. bodyweight of said individual per hour. In some embodiments, the dose infused is 0.25-7.5 nM of ST receptor ligand per 10 kg. bodyweight of said individual per hour. In some embodiments, the dose infused is 0.25-5 nM of ST receptor ligand per 10 kg. bodyweight of said individual per hour. In some embodiments, the dose infused is 0.25-2.5 nM of ST receptor ligand per 10 kg. bodyweight of said individual per hour. In some embodiments, the dose infused is 0.25-1.5 nM of ST receptor ligand per 10 kg. bodyweight of said individual per hour. In some embodiments, the dose infused is 0.25-1.0 nM of ST receptor ligand per 10 kg. bodyweight of said individual per hour. In some embodiments, the dose infused is 0.5-0.75 nM of ST receptor ligand per 10 kg. bodyweight of said individual per hour. In some embodiments, the dose infused is 0.25-0.5 nM of ST receptor ligand per 10 kg. bodyweight of said individual per hour. In some embodiments, the dose infused is 0.5-10 nM of ST receptor ligand per 10 kg. bodyweight of said individual per hour. In some embodiments, the dose infused is 0.5-7.5 nM of ST receptor ligand per 10 kg. bodyweight of said individual per hour. In some embodiments, the dose infused is 0.5-5 nM of ST receptor ligand per 10 kg. bodyweight of said individual per hour. In some embodiments, the dose infused is 0.5-2.5 nM of ST receptor ligand per 10 kg. bodyweight of said individual per hour. In some embodiments, the dose infused is 0.5-1.5 nM of ST receptor ligand per 10 kg. bodyweight of said individual per hour. In some embodiments, the dose infused is 0.5-1.0 nM of ST receptor ligand per 10 kg. bodyweight of said individual per hour. In some embodiments, the dose infused is 0.5-0.75 nM of ST receptor ligand per 10 kg. bodyweight of said individual per hour. In some embodiments, the dose infused is 0.75-10 nM of ST receptor ligand per 10 kg. bodyweight of said individual per hour. In some embodiments, the dose infused is 0.75-7.5 nM of ST receptor ligand per 10 kg. bodyweight of said individual per hour. In some embodiments, the dose infused is 0.75-5 nM of ST receptor ligand per 10 kg. bodyweight of said individual per hour. In some embodiments, the dose infused is 0.75-2.5 nM of ST receptor ligand per 10 kg. bodyweight of said individual per hour. In some embodiments, the dose infused is 0.75-1.5 nM of ST receptor ligand per 10 kg. bodyweight of said individual per hour. In some embodiments, the dose infused is 0.75-1.0 nM of ST receptor ligand per 10 kg. bodyweight of said individual per hour. In some embodiments, the dose infused is 1-10 nM of ST receptor ligand per 10 kg. bodyweight of said individual per hour. In some embodiments, the dose infused is 1-7.5 nM of ST receptor ligand per 10 kg. bodyweight of said individual per hour. In some embodiments, the dose infused is 1-5 nM of ST receptor ligand per 10 kg. bodyweight of said individual per hour. In some embodiments, the dose infused is 1-2.5 nM of ST receptor ligand per 10 kg. bodyweight of said individual per hour. In some embodiments, the dose infused is 1-1.5 nM of ST receptor ligand per 10 kg. bodyweight of said individual per hour. In some embodiments, the dose infused is 1.5-10 nM of ST receptor ligand per 10 kg. bodyweight of said individual per hour. In some embodiments, the dose infused is 1.5-7.5 nM of ST receptor ligand per 10 kg. bodyweight of said individual per hour. In some embodiments, the dose infused is 1.5-5 nM of ST receptor ligand per 10 kg. bodyweight of said individual per hour. In some embodiments, the dose infused is 1.5-2.5 nM of ST receptor ligand per 10 kg. bodyweight of said individual per hour. In some embodiments, the dose infused is 2.5-10 nM of ST receptor ligand per 10 kg. bodyweight of said individual per hour. In some embodiments, the dose infused is 2.5-7.5 nM of ST receptor ligand per 10 kg. bodyweight of said individual per hour. In some embodiments, the dose infused is 2.5-5 M of ST receptor ligand per 10 kg. bodyweight of said individual per hour. In some embodiments, the dose infused is 5-10 nM of ST receptor ligand per 10 kg. bodyweight of said individual per hour. In some embodiments, the dose infused is 5-7.5 nM of ST receptor ligand per 10 kg. bodyweight of said individual per hour.

In some embodiments, the ST receptor ligand is infused into the individual for at least 8 hours. In some embodiments, the ST receptor ligand is infused into the individual for at least 12 hours. In some embodiments, the ST receptor ligand is infused into the individual for at least 16 hours. In some embodiments, the ST receptor ligand is infused into the individual for at least 20 hours. In some embodiments, the ST receptor ligand is infused into the individual for at least 24 hours.

In some embodiments, a pharmaceutical composition is provided which comprises sterile, pyrogen free ST receptor ligand in an amount sufficient for continuous infusion of at least 0.1-10 nM of ST receptor ligand per hour for at least 6 hours, in some embodiments at least 12 hours, in some embodiments at least 16 hours, in some embodiments at least 20 hours and in some embodiments at least 24 hours. In some embodiments, a pharmaceutical composition is provided which comprises sterile, pyrogen free ST receptor ligand in an amount sufficient for continuous infusion of at least 0.1-10 nM of ST receptor ligand per hour for at least 6 hours, in some embodiments at least 12 hours, in some embodiments at least 16 hours, in some embodiments at least 20 hours and in some embodiments at least 24 hours. In some embodiments, a pharmaceutical composition is provided which comprises sterile, pyrogen free ST receptor ligand in an amount sufficient for continuous infusion of at least 0.1-10 nM of ST receptor ligand per hour for at least 6 hours, in some embodiments at least 12 hours, in some embodiments at least 16 hours, in some embodiments at least 20 hours and in some embodiments at least 24 hours.

In a preferred embodiment, the ST receptor ligand is the *E. coli* heat stable enterotoxin (ST), in its native form or modified to inhibit degradation, and the proper concentration of ST in the circulation is achieved by administering a continuous infusion of at least 0.5 micrograms per 10 kg. bodyweight of the individual per hour for at least 6 hours. In some embodiments, the ST is initially administered to an individual in a loading dose of at least 1 microgram of ST per 10 kg. bodyweight of the individual. In some embodiments, the loading dose is 1-10 micrograms of ST per 10 kg. bodyweight of the individual. In some embodiments, the loading dose is 3-5 micrograms of ST per 10 kg. bodyweight of the individual. In some embodiments, the loading dose is about 4 micrograms of ST per 10 kg. bodyweight of the individual. In some embodiments, the ST is infused into the individual in a dose of 0.5-8 micrograms of ST per 10 kg. bodyweight of the individual. In some embodiments, the ST is infused into the individual in a dose of 1-5 micrograms of ST per 10 kg. bodyweight of the individual. In some embodiments, the ST is infused into the individual in a dose of about 3 micrograms of ST per 10 kg. bodyweight of the individual. In some embodiments, the ST is infused into the individual for at least 8 hours. In some embodiments, the ST is infused into the individual for at least 12 hours. In some embodiments, the ST is infused into the individual for at least 16 hours. In some embodiments, the ST is infused into the individual for at least 20 hours. In some embodiments, the ST is infused into the individual for at least 24 hours. In some embodiments, the ST is infused into the individual for 12-24 hours.

In a preferred embodiment, the ST ligand is the *E. coli* heat stable enterotoxin (ST) and the proper concentration of ST in the circulation is achieved by administering a loading dose of about 30 micrograms of ST, and a continuous infusion of 20 micrograms per hour for a 70 kg individual. A continuous infusion is administered to maintain the plasma concentration of ST greater than $10^{-9}$ M. The infusion is continued for at least 12 hours and up to 24 hours.

After the infusion has been completed, the number of the patient's colorectal, gastric and esophageal cancer cells decreases, and imaging or therapy with a compound targeted by ST or another agent which binds to ST receptors is initiated.

The ability to inhibit the proliferation of cancer cells has been demonstrated with T84 and Caco 2 human colon carcinoma cells after exposure to STa and uroguanylin In embodiments of the present invention in which patients with metastatic colorectal and primary and metastatic gastric and esophageal cancer are treated or their cancer tumors are imaged, the ST receptor targeted therapeutic or imaging compounds are administered following initiation of the method of inhibiting proliferation of the cancer cells. Thus, generally before imaging or therapeutic agents targeted with ST receptor-binding compounds are employed in a patient with colorectal or primary or metastatic gastric or esophageal cancer, the patient is pretreated to inhibit the proliferation of the cancer cells. The actual timing of administration of the ST receptor ligand and the active ST receptor binding compounds relative to each other is not critical. Rather, the methods require that the sustained presence of an ST receptor ligand occur for a period sufficient to inhibit the proliferation of cancer cells and the active compound which binds to ST receptors is administered at such time to be present in the body after the number of cells has begun to decrease.

In some embodiments, therapeutic compounds which comprise a ST receptor binding compound such as an ST receptor binding peptide and a cytotoxic or cytostatic agent, including radioactive and radiostable agents, such as those disclosed in U.S. Pat. Nos. 5,518,888, 5,879,656, 6,060,037, and 6,268,159, and PCT application number PCT/US94/12232 are administered following or contemporaneous with inhibition of proliferation of the cancer cells. In some embodiments, the method of treating an individual who has metastasized colorectal or primary or metastatic gastric or esophageal cancer comprises the steps of first inhibiting proliferation of cancer cells in the individual by administering to said individual by substantially continuous infusion, at least 0.1-10 nM of an ST receptor ligand per 10 kg. bodyweight of the individual per hour for at least 6 hours. A therapeutic pharmaceutical composition that comprises components which target ST receptor for delivery of a therapeutic agent is then administered to the individual. In some embodiments, the therapeutic pharmaceutical composition comprises a conjugated composition that comprises an ST receptor binding moiety and an active moiety which is a therapeutic agent. In some embodiments, the ST receptor binding moiety is a peptide. In some embodiments, the ST receptor binding moiety is selected from the group consisting of SEQ ID NO:2, SEQ ID NO:3, SEQ ID NOS:5-56 and fragments and derivatives thereof. In some embodiments, the therapeutic agent is radioactive. In some embodiments, the therapeutic agent is selected from the group consisting of $^{43}$K, $^{52}$Fe, $^{57}$Co, $^{67}$Cu, $^{67}$Ga, $^{68}$Ga, $^{77}$Br, $^{81}$Rb/$^{81M}$Kr, $^{87M}$Sr, $^{166}$Ho, $^{211}$Bi, $^{153}$SM, $^{113}$IN, $^{123}$I, $^{125}$I, $^{127}$CS, $^{129}$CS, $^{131}$I, $^{132}$I, $^{197}$Hg, $^{203}$Pb and $^{206}$Bi. In some embodiments, the therapeutic agent is selected from the group consisting of: $^{47}$Sc, $^{67}$Cu, $^{90}$Y, $^{109}$Pd, $^{123}$I, $^{125}$I, $^{131}$I, $^{186}$Re, $^{188}$Re, $^{199}$Au, $^{211}$At, $^{212}$Pb, $^{212}$B, $^{32}$P and $^{33}$P, $^{71}$Ge, $^{77}$As, $^{103}$Pb, $^{105}$Rh, $^{111}$Ag, $^{119}$Sb, $^{121}$Sn, $^{131}$CS, $^{143}$Pr, $^{161}$Tb, $^{177}$Lu, $^{191}$Os, $^{193M}$Pt and $^{197}$Hg. In some embodiments, the therapeutic agent is radiostable. In some embodiments, the therapeutic agent is selected from the group consisting of: compounds that cause cell death, compounds that inhibit cell division, and compounds that induce cell differentiation. In some embodiments, the therapeutic agent is selected from the group consisting of: chemotherapeutics, toxins and radiosensitizing agents. In some embodiments, the therapeutic agent is selected from the group consisting of: methotrexate, doxorubicin, daunorubicin, cytosinarabinoside, etoposide, 5-4 fluorouracil, melphalan, chlorambucil, cis-platin, vindesine, mitomycin, bleomycin, purothionin, macromomycin, 1,4-benzoquinone derivatives, trenimon, ricin, ricin A chain, *Pseudomonas* exotoxin, diphtheria toxin, *Clostridium perfringens* phospholipase C, bovine pancreatic ribonuclease, pokeweed antiviral protein, abrin, abrin A chain, cobra venom factor, gelonin, saporin, modeccin, viscumin, volkensin, nitroimidazole, metronidazole, misonidazole, porfimer and compounds that enchance the accumulation of intracellular cGMP such as phosphodiesterase inhibitors, for example exisulind, zaprinast, and sildenafil.

In some embodiments, detectable compounds which comprise a ST receptor binding compound such as an ST receptor binding peptide and a detectable agent such as those disclosed in U.S. Pat. Nos. 5,518,888, 5,879,656, 6,060,037, and 6,268,159, and PCT application number PCT/US94/12232 are administered following or contemporaneous with the inhibition of proliferation of cells expressing the ST receptor protein. In some embodiments, the method of imaging a metastasized colorectal tumor or primary or metastatic gastric or esophageal tumor in an individual who has metastasized colorectal or primary or metastasized gastric or esophageal cancer comprises the step of first inhibiting the proliferation of cancer cells in the individual by administering to the individual by substantially continuous infusion, at least 0.1-10 nM of an ST receptor ligand per 10 kg. bodyweight of the individual per hour for at least 6 hours. A pharmaceutical imaging composition that comprises components which target ST receptor for delivery of an imaging agent is then administered to the individual. In some embodiments, the imaging is performed by radioscintigraphy, nuclear magnetic resonance imaging (MRI) or computed tomography (CT scan). In some embodiments, the pharmaceutical imaging composition comprises a conjugated composition that comprises an ST receptor binding moiety and an active moiety that is an imaging agent. In some embodiments, the ST receptor binding moiety is a peptide. In some embodiments, the ST receptor binding moiety is selected from the group consisting of SEQ ID NO:2, SEQ ID NO:3, SEQ ID NOS:5-56 and fragments and derivatives thereof. In some embodiments, the imaging agent is radioactive. In some embodiments, the therapeutic agent is selected from the group consisting of: $^{43}$K, $^{52}$Fe, $^{57}$Co, $^{67}$Cu, $^{67}$Ga, $^{68}$Ga, $^{77}$Br, $^{81}$Rb/$^{81M}$Kr, $^{87M}$Sr, $^{99M}$Tc, $^{111}$In, $^{113M}$In, $^{123}$I, $^{125}$I, $^{127}$Cs, $^{129}$Cs, $^{131}$I, $^{132}$I, $^{197}$Hg, $^{203}$Pb and $^{206}$Bi. In some embodiments, the therapeutic agent is selected from the group consisting of: $^{47}$Sc, $^{67}$Cu, $^{90}$Y, $^{109}$Pd, $^{123}$I, $^{125}$I, $^{131}$I, $^{186}$Re, $^{188}$Re, $^{199}$Au, $^{211}$At, $^{212}$Pb, $^{212}$B, $^{32}$P and $^{33}$P, $^{71}$Ge, $^{77}$As, $^{103}$Pb, $^{105}$Rh, $^{111}$Ag, $^{119}$Sb, $^{121}$Sn, $^{131}$Cs, $^{143}$Pr, $^{161}$Tb, $^{177}$Lu, $^{191}$Os, $^{193M}$Pt and $^{197}$Hg. In some embodiments, the imaging agent is radiostable. In some embodiments, the imaging agent is a heavy metal such as iron chelates, or chelates of gadolinium or manganese. In some embodiments, the imaging is performed by positron emission tomography (PET) using positron emitters of oxygen, nitrogen, iron, carbon, or gallium. In other embodiments, the imaging is performed by light imaging dyes such as pthallocyanine derivatives and indocyanine derivatives.

In some embodiments, compounds which comprise an ST receptor binding compound such as an ST receptor binding peptide and an active agent such as those disclosed in U.S. Pat. Nos. 5,518,888, 5,879,656, 5,962,220, 6,060,037, 6,087,109 and 6,268,159, PCT application number PCT/US94/12232 and Ser. No. 08/467,920 filed Jun. 6, 1995 are administered following or contemporaneous with inhibition of proliferation of cells expressing the ST receptor protein. In some embodiments, the method of treating an individual who has a genetic disease, a predisposition for a genetic disease, metastasized colorectal or primary or metastasized gastric or esophageal cancer comprises the steps of first inhibiting the proliferation of cancer cells in the individual by administering to said individual by oral or rectal administration, at least 0.1-10 nM of n ST receptor ligand per 10 kg. bodyweight of the individual per hour for at least 6 hours. A pharmaceutical composition that comprises components which target ST receptor for delivery of an active agent, such as a gene therapeutic, antisense compound, or ribozyme is then administered to the individual. In some embodiments, the pharmaceutical composition comprises a conjugated composition that comprises an ST receptor binding moiety and an active moiety which is a therapeutic agent.

In embodiments of the present invention, individuals are being screened for the detection of evidence of ST receptor gene expression in extraintestinal samples, such as by those methods described U.S. Pat. Nos. 5,601,990, 5,731,159, 5,928,873, and 6,060,037, PCT application number PCT/US94/12232, and PCT application No. PCT/US97/07467, the detection of which in such samples indicates metastasized colorectal cancer or primary or metastasized gastric or esophageal cancer. In such embodiments, the individuals are administered parenterally ST receptor ligand in sufficient quantity for sufficient time to inhibit proliferation of cancer cells of colorectal, gastric or esophageal origin.

Following initiation of the method of inhibiting proliferation, the extraintestinal samples are obtained and screened for evidence of ST receptor expression. Generally, assays to detect ST receptor protein, mRNA encoding ST receptor protein or cDNA generated from such mRNA are typically the evidence whose presence is detected. Before samples are obtained, the patient is typically pretreated to inhibit proliferation of colorectal, gastric and esophageal cancer cells. The actual timing of administration of the ST receptor ligand and the active ST receptor binding compounds relative to each other is not critical. Rather, the methods require that the sustained presence of an ST receptor ligand occur for a period sufficient to inhibit the proliferation of a cell and that the extraintestinal sample to be screened is obtained after the number of cells has decreased.

In some embodiments, the method of determining whether an individual has metastasized colorectal cancer or primary or metastasized gastric or esophageal cancer comprises the step of first increasing the number of ST receptor molecules on the surface of a cancer cell in the individual by administering to the individual by substantially continuous infusion, at least 0.1-10 nM of an ST receptor ligand per 10 kg. bodyweight of the individual per hour for at least 6 hours. A sample of extraintestinal body fluid and/or tissue is then obtained from the individual and an assay is run to detect the presence of protein or mRNA encoding ST receptor in the sample. The presence of the protein or mRNA indicates that the individual has metastatic colorectal cancer or primary or metastatic gastric or esophageal cancer. In some embodiments, the presence of the mRNA is detected using a polymerase chain reaction. In some embodiments, the extraintestinal sample is tissue or body fluid. In some embodiments, the extraintestinal sample is blood. In some embodiments, the extraintestinal sample is screened to detect the presence of ST receptor protein in the sample using an immunoassay.

EXAMPLES

Example 1

ST as an Anticancer Agent

ST is a cytostatic agent, but not an apoptotic or cytotoxic drug. It can be used alone or in combination therapies to treat: 1) adenomas and polyps of the small and large intestine; 2) intestinal and colorectal carcinomas and their metastases; 3) cancer recurrence of the gastrointestinal (GI) tract; 4) at-risk population for polyp and cancer of the GI tract.

The combination therapy is an alternative approach to the mono-therapy with ST and it has been conceived to maximize the tumor to normal cells toxicity ratio of the anti-neoplastic intervention. The combination therapy should include:

1. ST receptor ligand such as ST plus surgery;
2. ST receptor ligand such as ST plus one or more of the classic chemotherapeutic drugs (e.g. fluorouracil, leucovorin, cisplatin, levamisole, $H_2$ antagonists, folate);
3. ST receptor ligand such as ST plus one or more of the new anti-neoplastic drugs (e.g. genasense (Genta); SAHA (Aton Pharma), vitaxin (applied Molecular Evolution), EMD121974 (E-Merck));
4. ST receptor ligand such as ST plus one or more vitamins (e.g. vitamin D; vitamin A; vitamin C, vitamin E, β-carotene);
5. ST receptor ligand such as ST plus radiation therapy;
6. ST receptor ligand such as ST plus calcium (e.g. $CaCl_2$ 1 mM) and /or calcium mimics (e.g. cations as Barium, Nichel);
7. ST receptor ligand such as ST plus compounds that enchance the accumulation of intracellular cGMP such as phosphodiesterase inhibitors, for example exisulind, zaprinast, and sildenafil. (e.g. zaprinast 10 μM; dipyridamole 10 μM)
8. ST receptor ligand such as ST plus cyclic GMP analogs (e.g. 8-br-cGMP 5 mM; dibutyryl-cGMP 5 mM)
9. ST receptor ligand such as ST plus agonists of cyclic nucleotide gated (CNG) channels (e.g. 8-(4-chlorophenylthio)-cGMP 500 μM; 1000-2000PEG-$(cGMP)_2$ 1 μM);
10. ST receptor ligand such as ST plus cyclic AMP analogs (e.g. dibutyryl-cAMP 0.1 mM);
11. ST receptor ligand such as ST plus agents that causes intracellular mobilization of cyclic nucleotides (e.g. VIP 10 nM, forskolin 1 μM, NO donors);
12. ST receptor ligand such as ST plus calcium influx inhibitors (e.g. carboxymido-triazole (CAI) 2.3 μM);
13. ST receptor ligand such as ST plus inhibitors of store-operated calcium entry (e.g. $La^{3+}$ 100 μM, N-1-n-octyl-3,5-bis-(4-pyridyl)triazole (DPT) 10 μM, SFK 96364);
14. ST receptor ligand such as ST plus non-steroidal anti-inflammatory drugs (NSAIDs) (e.g. acetyl-salicylic-acid 2 mM, mefenamic acid 200 μM, sulindac sulfide 60 μM);
15. ST receptor ligand such as ST plus sulindac derivatives (e.g. sulindac sulfone (exisulind) 0.6 mM, CP248 1 μM, CP461 10 μM).

Routes of Administration:

ST receptor ligand such as ST should be administered parentally as anti-neoplastic drug. Oral administration should be avoided for the hyper-secretory and diarrheic effect of ST receptor ligand in the intestine. Depending on disease staging and metastasis spreading, ST receptor ligand could be administered intravenously (I.V.), subcutaneously, intramuscularly, intraperitoneally or intrathecally. In addition, ST receptor ligand could be administered regionally via direct injection into the main artery supplying the diseased organ.

ST Dosages for Mono-and Combination Therapy

The $IC_{50}$ for ST as an anticancer agent in vitro is 14 nM

The predicated target concentration for ST in vivo is 140 nM

I.V. Loading Dose (bolus dose) for a 70 Kg patient is 3.3 mg

I.V. Maintenance Dose (infusion rate) is 1 μg/min/Kg (equivalent to 4.3 mg/hour for a 70 Kg patient)

Dosage Regimens

1. Continuous infusion (infusion rate: 1 μg/min/Kg) for a minimum of 7 days up to a maximum of 15 day, with a 7 day interval periods during which the patients undergo to a chemotherapy treatment with a cytotoxic drug (e.g. fluorouracil, cisplatin, etc.) A mini-pump system may be employed for I.V. infusions.

2. Intermittent dosage regimens with morning (7-9 a.m.) single dose of 3.3 mg every 24 h for 30 consecutive days. This 30-day treatment can be repeated after 15-day intervals during which patients can be dosed with cytotoxic drugs (e.g. fluorouracil, cisplatin, etc.)

Example 2

The heat stable enterotoxin, ST, has been demonstrated to induce a prolongation of the cell cycle (a cytostatic effect). This cytostatic effect is specific to cells expressing guanylyl cyclase C, such as cancer cells from colorectal, gastric and esophageal adenocarcinomas. When used in conjunction with standard chemo-(5FU, irenotecan, leukovorin, etc) or radiation (external bean, targeted radiotherapy, etc.) therapies, the therapeutic index of these standard therapies will be enhanced due to the ability to achieve a similar clinical response at a lower cytotoxin dose. This concept applies equally to the use of ST and all GCC ligands, irrespective of their structure or origin Pre-clinical data has shown that the overall cell cycle time is slowed, yet no particular phase was favored over another after ST treatment of GCC-bearing cells. Data from the effect of treatment with ST alone on cell cycle indicates that the time spent in various phases of the cell cycle increases equally for all four phases of the cell cycle as a result of ST treatment. Data from the effect of treatment with ST plus doxorubicin on cell cycle indicates a profound shift whereby the cell does not progress through the cell cylce. The implications of this finding is that ST can be used as a cytostatic drug in combination with current chemotherapies, decreasing their adverse side effects while maintaining the same therapeutic effect (an improved therapeutic index). A combination of ST with phase-specific therapeutics, such as 5-Fluorouracil, enhances killing of cells as they spend more time in the S phase. As a result, the proportion of cells existing in other phases would be modified and they could then be attacked either with prolonged 5-Fluorouracil therapy or by adjunct therapy using a different cytotoxin, such as bleomycin, which selectively kills those cells in G1 phase. This latter approach, wherein, different cytotoxins are used in conjunction with ST in an alternating regimen may be preferable to avoid the selective survival of cytotoxin-resistant cells.

Information in Table 1 reflects dosage calculations. A sample dosage regimen in humans is described below. ST is used to attain an acute cytostatic effect by bolus injection or to maintain this effect indefinitely by continuous infusion following the bolus injection.

TABLE 1

| Item | Measure | Reference |
|---|---|---|
| Molecular weight of ST | 1972 g/mole | Primary technical literature |
| $EC_{50}$ for ST | 10 nM | In vitro TJU experiments |
| Colorectal cancer patient | 70 kg; blood volume = 5.5 liters; 12 liters ECF volume | Goodman & Gilman |
| Blood half-life for ST (rat) | 6 min ($\alpha$); 2.68 hrs ($\beta$) | data |
| Blood half-life for ST (man) | 24 min ($\alpha$); 11.12 hrs ($\beta$) | Allometric scaling theory |
| Clearance | 14.9 $hr^{-1}$ in rats (Primarily renal) | data |
| Volume of distribution, $V_d$ | 49 mls in rats (An ECF agent) | data |

Calculations of Dosages:

To achieve therapeutic efficacy, the steady state concentration ($C_{ss}$) should be $\geq 10$ $EC_{50}$. This is readily attained by multiple dosage regimens, three of which are illustrated below. Additionally, combinations of methods A-C, or other regimens will serve to produce a therapeutic effect using ST.

Minimal Bolus Dose

From the above information, a bolus I.V. administration of 2.4 milligrams of ST (1.2 μmoles) as a loading dose will result in a target concentration of approximately 100 nM (10-fold higher than the $EC_{50}$), and the concentration in extracellular fluid should stay at or above the $EC_{50}$ for approximately 1.5 hours.

$$\text{Loading Dose} = (\text{Target Concentration})(\text{Volume of distribution})$$
$$= (100\text{ nM})(12\text{ liters}) = 1.2\ \mu\text{moles (2.4 milligrams)}$$

Maximal Bolus Dose

An amount of ST is injected intravenously to maintain the concentration at ≧10 $EC_{50}$ for a prolonged period of time to induce a therapeutic effect. It is known that the cell cycle effect of ST is instantaneous and cells take a complete cell cycle to full recover. Given this, it is reasonable to postulate that the therapeutic dose must be maintained for at least 6 hours to achieve a clinical effect: (24 hrs/cycle)/4 phases/cycle).

$$\text{Dose}=[(C_t)/e^{-kt}](V_d)$$

Where, $C_t$ is the concentration of ST at time "t"; equal to ≧10 $EC_{50}$ (≧100 nM).

$V_d$ is the volume of distribution of ST (12 liters)

k is the rate constant for ST elimination (k=0.693/half-life in minutes)

The $t_{1/2}$ (α) in man was calculated to be 24 minutes for ST.

The time to maintain this minimal concentration is 6 hours

Therefore, the bolus dose administered would need to be:

$ST=[(100\text{ nM})(12\text{ liters})]/e^{-(6.93\ hr-1)(6\ hrs)}=39.5$ millimoles (78 grams)

Continuous Intravenous Infusion

An alternative approach is to provide the patient with continual intravenous dosing of ST, thereby maintaining the cytostatic effect through adjuvant chemotherapy, while minimizing any adverse effects associated with ST. To achieve therapeutic efficacy, the steady state concentration ($C_{ss}$) should be ≧10 $EC_{50}$. To maintain a value of 10*$EC_{50}$ indefinitely ($C_{ss}$) would require an infusion rate of:

$$\text{Infusion Rate}=(\text{Target concentration})(\text{Clearance})t_{1/2}=0.53\text{ hours }(\alpha+\beta)$$

$$C1=(0.693)(V_d/70\text{ kg man})/(t1/2)=3.7\text{ ml/min/kg}$$

From this, $$\text{Infusion rate}=(100\text{ nM})(3.7\text{ ml/min/kg})=370\text{ pmoles/min/kg}$$

Or 25.9 nanomoles/min (51 micrograms/min) for a 70 kg man over a six hour period for a total of 184 milligrams administered.

Example 3

Bacterial Enterotoxins are Associated with Resistance to Colon Cancer

One half million patients suffer from colorectal cancer in industrialized nations, yet this disease exhibits a low incidence in under-developed countries. This geographic imbalance suggests an environmental contribution to the resistance of endemic populations to intestinal neoplasia. A common epidemiological characteristic of these colon cancer-spared regions is the prevalence of enterotoxigenic bacteria associated with diarrheal disease. Here, a bacterial heat-stable enterotoxin was demonstrated to suppress colon cancer cell proliferation by a guanylyl cyclase C-mediated signaling cascade. The heat-stable enterotoxin suppressed proliferation by increasing intracellular cGMP, an effect mimicked by the cell-permeant analog 8-br-cGMP. The antiproliferative effects of the enterotoxin and 8-br-cGMP were reversed by L-cis-diltiazem, a cyclic nucleotide-gated channel inhibitor, as well as by removal of extracellular Ca2+, or chelation of intracellular Ca2+. In fact, both the enterotoxin and 8-br-cGMP induced an L-cis-diltiazem-sensitive conductance, promoting Ca2+ influx and inhibition of DNA synthesis in colon cancer cells. Induction of this previously unrecognized antiproliferative signaling pathway by bacterial enterotoxin could contribute to the resistance of endemic populations to intestinal neoplasia, and offers a paradigm for targeted prevention and therapy of primary and metastatic colorectal cancer.

Colorectal cancer is the fourth leading cause of cancer and cancer-related mortality in the world, with a geographic distribution primarily affecting patients in developed countries (FIG. 1*a*; ref. 1). Although the epidemiology of this disease remains poorly understood, there is an unexplained inverse relationship between the incidence of colorectal cancer and enterotoxigenic *Escherichia coli* (ETEC) infections (FIG. 1*a*). Indeed, the age-adjusted incidence of colorectal cancer is lowest in under-developed countries (1), where ETEC infections are the highest (FIG. 1*a*; refs. 2 and 3).

ETEC produce heat-stable enterotoxins (STs; refs. 4 and 5), a principle cause of secretory diarrhea in endemic populations, travelers, and agriculturally important animal herds (6, 7). These enterotoxins are plasmid-encoded small (≦19 amino acids) peptides that bind to guanylyl cyclase C (GC-C), specifically expressed in intestinal epithelial cells (4, 8).

Association of STs with the extracellular domain of GC-C activates the intracellular catalytic domain that converts GTP into cGMP (9, 10). The second messenger cGMP, in turn, activates cGMP-dependent protein kinase (PKG) II, the conventional downstream effector for this cyclic nucleotide, resulting in secretory diarrhea (9-11). In this way, STs represent molecular mimicry wherein enterotoxigenic bacteria have evolved a strategy for dissemination and propagation that exploits normal intestinal physiology. Indeed, STs are structurally and functionally homologous to the endogenous peptides guanylin and uroguanylin (12, 13), which mediate autocrine/paracrine control of intestinal fluid and electrolyte homeostasis (14).

Beyond volume homeostasis, GC-C and its ligands have been implicated in the regulation of the balance of proliferation and differentiation along the crypt-to-villus axis in the intestine (15). Expression of endogenous GC-C ligands is frequently lost during tumorigenesis, and subsequent loss of signaling may represent one key mutational event underlying neoplastic transformation in the colon (16-18). In principle, this putative role for GC-C as a tumor suppressor may contribute to the inverse epidemiological association between colorectal cancer (1) and ETEC infections (2, 3) reflecting, in part, longitudinal exposure in under-developed countries to ST-producing bacteria. However, the mechanisms by which STs repress colorectal tumorigenesis are unknown. The present study revealed a previously unrecognized ST-induced cGMP-dependent signaling pathway, through cyclic nucleotide-gated (CNG) channels and calcium, responsible for the antiproliferative action of bacterial enterotoxins on human colon carcinoma cells.

Materials and Methods

Cell Culture.

T84 (passages 50-70) and SW480 (passage 100-120) human colon carcinoma cells, obtained from the American Type Culture Collection, were maintained at 37° C. (5% $CO_2$) in DMEM/F12 containing 2.5 mM L-glutamine, 100 units/ml penicillin, 100 μg/ml streptomycin, and 10% (vol/vol) FBS.

DNA Synthesis.

Exponentially growing cancer cells (~60% confluent in 96-well plates) were synchronized by serum starvation in Eagle's minimal essential medium (EMEM) for 48 h, followed by proliferative induction with 10 mM L-glutamine (in EMEM) for 24 h. ST and other agents were added to cells 15 min before 0.2 μCi per well (1 Ci=37 GBq) of [methyl-3H] thymidine, which was added for 3 h, followed by quantification of [3H]thymidine incorporation into DNA (15).

Current Measurements.

The perforated mode of the whole-cell patch-clamp recording was applied to human T84 colon cancer cells. Membrane potential was controlled through the electrical access obtained by membrane perforation induced by amphotericin B (9, 10). The pipette solution supplemented by amphotericin B (200-240 mg/ml) contained: 140 mM KCl, 1 mM $MgCl_2$, 5 mM EGTA, and 20 mM Hepes-KOH (pH 7.3). The bath solution contained (in mM): 136.5 mM NaCl, 5.4 mM KCl, 1.8 mM $CaCl_2$, 0.5 mM $MgCl_2$, 5.5 mM glucose, and 5 mM Hepes-NaOH (pH 7.4). Voltage-clamp recordings were performed with an Axopatch 1-C patch-clamp amplifier (Axon Instruments, Foster City, Calif.) at 31±1° C. using an HCC-100 temperature controller (Dagan Instruments, Minneapolis; ref. 19).

Cyclic Nucleotides.

cGMP and cAMP were quantified in exponentially growing T84 cells (~60% confluent in 96-well plates) employing ELISA (Amersham Pharmacia) or RIA. In experiments employing ELISA, media was aspirated, reactions were terminated by the addition of a lysis solution (200 μl per well) containing 0.5% dodecyltrimethylammonium bromide, and aliquots (100 μl) from each well were processed for cyclic nucleotide determinations. In experiments employing RIA, reactions were terminated with ice-cold 100% ethanol, and supernatants were separated from pellets by centrifugation and processed for cGMP determinations (8).

Calcium Transport.

Exponentially growing T84 cells (40-80% confluent in 24-well plates) were incubated in media (S-MEM, Life Technologies, Rockville, Md.) containing low (300 μM) $CaCl_2$ to maximize the signal-to-noise ratio for L-cis-diltiazem (L-DLT)-sensitive $45Ca^{2+}$ transport determinations. Cells were treated with ST, 8-br-cGMP, and/or L-DLT for the indicated times, followed by the addition of 1 μCi per well $45Ca^{2+}$ for the last 15 min. Incubations were terminated by washing four times in cold PBS buffer (145 mM NaCl/5 mM KCl/1 mM $MgCl_2$/10 mM glucose/5 mM Hepes, pH 7.4) containing 0.1 mM EGTA, cells were solubilized with cold NaOH (0.1 M), and radioactivity was quantified in 100-μl aliquots.

Results and Discussion

ST inhibited DNA synthesis in human colon cancer cells that express GC-C, but not in tumor cells deficient in GC-C (FIG. 1b). The concentration-dependence of ST inhibition of proliferation corresponded to the accumulation of intracellular cGMP [cGMP]i, but not other cyclic nucleotides (FIG. 1c). Yet, selective inhibitors of PKG, which disrupt ST induction of intestinal secretion (20), did not prevent the antiproliferative action of the enterotoxin (FIG. 1d). Moreover, inhibitors of cAMP-dependent protein kinase or cGMP-regulated phosphodiesterase 3 did not influence inhibition of proliferation by ST (FIG. 1d). Thus, the antiproliferative actions of ST on human colon carcinoma cells were not mediated by conventional downstream effectors of cGMP.

Figure 3B:
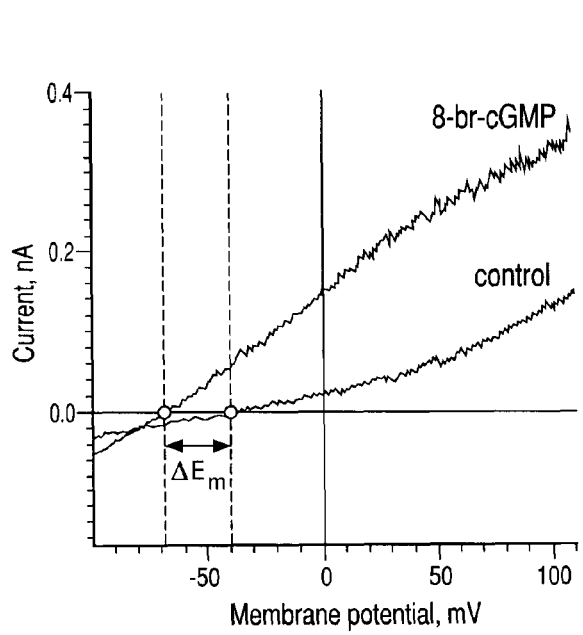
Figure 3C:
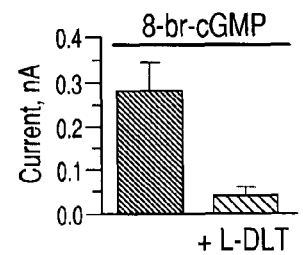
Figure 3D:
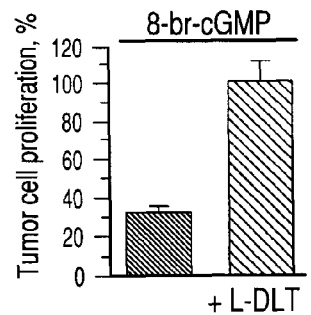

Rather, a specific reversible inhibitor of CNG channels, L-DLT (21), prevented ST inhibition of proliferation (FIG. 1d). In fact, ST induced membrane current in voltage-clamped human colon cancer cells that was reversibly blocked by L-DLT, indicating that the enterotoxin activates CNG channels (FIGS. 2a and 2b). Throughout the range of the imposed membrane potential ramp, ST significantly increased current, an effect largely reversed by L-DLT (FIG. 2c). Although the reversal potential (Em) of colon cancer cells was −39.3±3.9 mV (n=6), ST shifted Em to −66.3±3.6 mV (n=6; FIG. 2c), an effect abolished by L-DLT that restored Em to −39.5±5.2 mV (n=4; FIG. 2c). The action of ST on membrane current in colon cancer cells was mimicked by the membrane-permeant cGMP analog, 8-br-cGMP, which also induced an L-DLT-sensitive current and produced a significant shift in Em (ΔEm=−25.8±4.6 mV, n=3; FIGS. 3a-c). Moreover, 8-br-cGMP inhibited tumor cell DNA synthesis in an L-DLT sensitive manner (FIG. 3d). Identical actions of ST and 8-br-cGMP in colon cancer cells demonstrate that a [cGMP]i-signaling pathway mediates the action of the enterotoxin on activation of CNG channels and suppression of tumor cell proliferation.

Figure 4A:
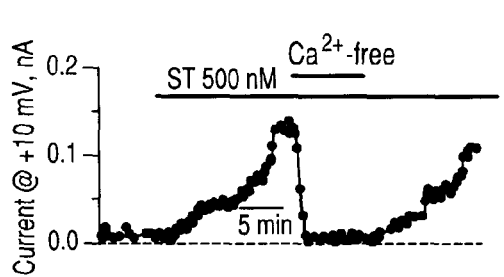
FIGS. 4a-4f show ST and 8-br-cGMP alter the membrane conductance and proliferation of human colon carcinoma cells by inducing CNG channel-mediated calcium influx.
Figure 4B:
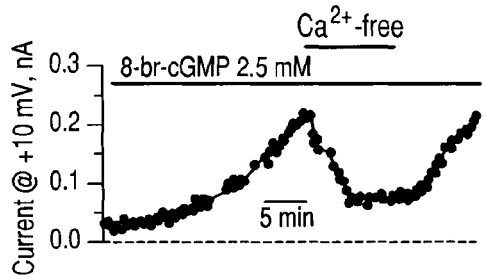
Figure 4C:
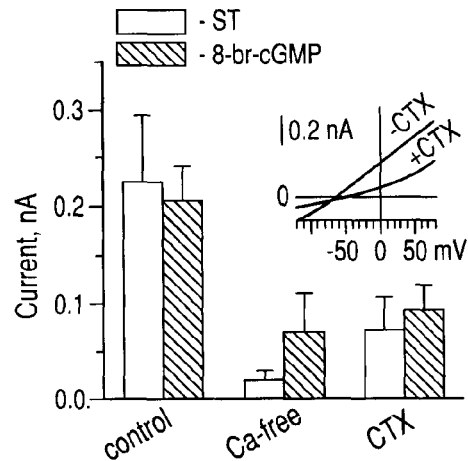
Figure 4D:
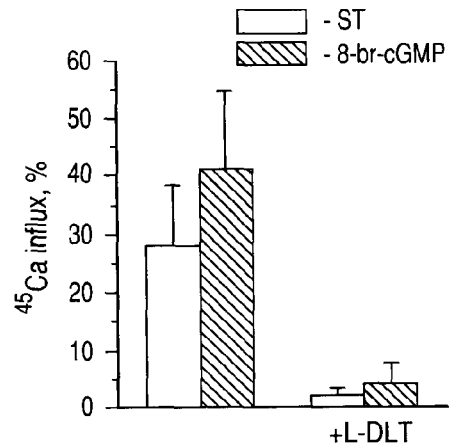

The nonselective CNG channel preferentially conducts $Ca^{2+}$ ions (22). Accordingly, removal of extracellular $Ca^{2+}$ ($[Ca^{2+}]ext$) reduced both ST and 8-br-cGMP currents, from 0.23±0.07 to 0.02±0.01 nA and from 0.21±0.04 to 0.07±0.04 nA, respectively (n=5; FIG. 4a-c). As a further indicator of Ca2+ entry, Ca2+–dependent K+current (KCa), previously reported in this cancer cell line (23) and identified here by sensitivity to the specific blocker charybdotoxin, was found to be induced by both ST and 8-br-cGMP (FIG. 4c). In accordance, reversal potentials derived from the ST- and 8-br-cGMP-induced current-voltage relationships approached −70 mV (FIGS. 2c, 3b, and 4c Inset), which closely approximates the theoretical equilibrium potential for K+ ions (EK∼−75 mV) calculated from the Nernst equation (24). Such shift in Em away from Ca2+ equilibrium would drive Ca2+ influx. However, failure to exactly match the theoretical K+ equilibrium reflects current contribution by non-K+ conductances, such as the chloride-carrying CFTR and/or non-selective current through CNG channels. Finally, ST and 8-br-cGMP-mediated Ca2+ entry through CNG channels was demonstrated by direct measurement of radioactive calcium flux into colon cancer cells that was inhibited by L-DLT (FIG. 4d).

Figure 4E:
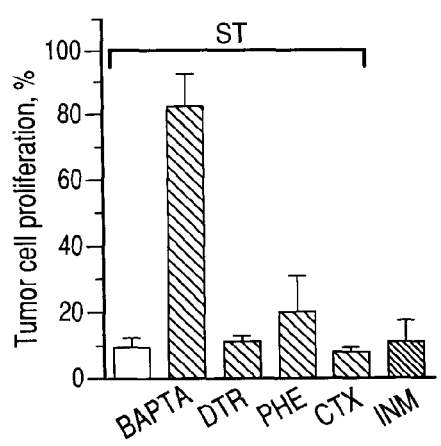
Figure 4F:
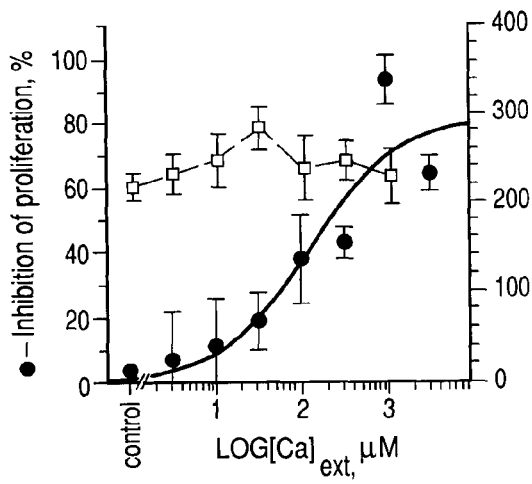

The essential role of Ca2+ influx in the ST-mediated regulation of cancer cell proliferation is underscored by reversal of ST antiproliferative action through cytosolic Ca2+ chelation with BAPTA-AM (FIG. 4e). Furthermore, without influencing [cGMP]i, depletion of [Ca2+]ext abolished the ability of ST to inhibit cancer cell proliferation, whereas increases in [Ca2+]ext restored in a concentration-dependent manner the antiproliferative effect of ST (FIG. 4f). In fact, ionomycin, a Ca2+ ionophore, mimicked, whereas dantrolene, which blocks Ca2+ release from intracellular pools, or phenamil, an inhibitor of electrogenic Na+ influx, did not affect the ability of ST to inhibit cancer cell proliferation (FIG. 4e). The absence of charybdotoxin effect on ST inhibition of cancer cell proliferation further indicates that Ca2+ entry rather than the consequent Ca2+-sensitive K+current is required for enterotoxin-mediated antiproliferation (FIG. 4e). Thus, ST inhibits DNA synthesis in colon carcinoma cells by a signaling mechanism initiated by activation of GC-C, accumulation of [cGMP]i, and Ca2+ influx through CNG channels.

cGMP is emerging as an important regulator of cell proliferation, although the molecular mechanisms mediating that activity appear to be varied and cell-specific. Thus, in human vascular smooth muscle cells, cGMP delays the G1/S transition by down-regulation of cyclin D1 and cyclin-dependent kinase 4 activities after platelet-derived growth factor stimulation (25). Also, cGMP suppresses human T cell proliferation by inhibiting IL-2 release (26). In addition, proliferation of glomerular mesangial cells by phorbol 12,13-dibutyrate-mediated activation of mitogen-activated protein kinase is antagonized by cGMP-induced expression of the specific phosphatase MKP-1 (27). Further, in colorectal cancer cells, the antiproliferative effects of cGMP may reflect activation of apoptotic pathways (28, 29) or regulation of cell cycle (15). Conversely, cGMP-dependent activation of PKG promotes human umbilical vein endothelial cell proliferation by stimulating Raf-1 kinase activity (30).

In the present study, proliferation of intestinal epithelial cells was suppressed by a signaling mechanism initiated by ST interaction with GC-C. Indeed, cells that lack this receptoenzyme molecule and do not exhibit ST-induced accumulation of [cGMP]i (31) were unresponsive to the antiproliferative effects of ST. ST/GC-C interaction induced the accumulation of [cGMP]i, which mediated suppression of proliferation by activating CNG channels. It is notable that cGMP inhibition of proliferation in intestinal cells is mediated through the L-DLT-sensitive CNG pathway, because specific inhibitors of cAMP-dependent protein kinase (32), phosphodiesterase 3 (11), and PKG (20), which mediate GC-C-dependent secretion, did not alter the effect of ST on DNA synthesis. Thus, ST-mediated [cGMP]i accumulation does not cause functional transactivation of cAMP-dependent pathways because ST did not induce [cAMP]i accumulation (FIG. 1c), activation of cAMP-dependent protein kinase, or inhibition of phosphodiesterase 3 (FIG. 1d). This report details the regulation of cell proliferation by a cGMP-dependent mechanism mediated by CNG channels.

Ca2+ serves as the third messenger in the signaling cascade linking GC-C at the cell surface to regulation of proliferation in the nucleus. Indeed, the ability of the second messenger cGMP to inhibit DNA synthesis was mediated by [Ca2+]ext influx through CNG channels (see FIGS. 4d-f). cGMP-dependent CNG channel-mediated Ca2+ influx has been described in excitable cells, although it mediates different functions. In this way, in cone and rod photoreceptors, high [cGMP]i sustains dark-state functions, in part, by inducing Ca2+ influx through CNG channels (33). Similarly, in the brain, cGMP-dependent activation of CNG channels regulates neurotransmitter release and potentiates synaptic transmission through Ca2+ influx (34). Additionally, regulation of intracellular Ca2+ by cGMP has been described in several cell systems, including vascular smooth muscle (35), platelets (36), and neurons (37). In intestinal cells, ST activation of GC-C mobilizes intracellular Ca2+ by a cGMP-dependent mechanism (38, 39). Further, ST and 8-br-cGMP induce Ca2+ influx through CNG channels in colon (40). In close agreement, the present study demonstrates that ST and 8-br-cGMP induce a structurally and functionally compartmentalized influx of Ca2+ through CNG channels in human colon carcinoma cells. Indeed, cGMP does not evoke electrophysiologically detectable Ca2+ currents in these cells (41), although its influx could be detected with radioactive Ca2+. The precise mode of Ca2+ delivery to its intracellular site of action to induce intestinal cell cytostasis remains undefined. Yet, this antiproliferative process must be tightly regulated because Ca2+ can, upon intracellular accumulation, promote apoptosis (42), which is not induced by ST (15).

In summary, these data demonstrate that bacterial enterotoxins suppress colon carcinoma cells through a GC-C-based calcium-dependent signaling pathway with a newly identified role in regulating cell proliferation. Endogenous GC-C ligands, guanylin and uroguanylin, may activate this pathway and promote the transition from proliferation to differentiation of enterocytes along the crypt-villus axis in normal intestine (15). In addition, these observations offer a possible mechanistic insight into the resistance to colorectal cancer observed in geographic areas in which ETEC is endemic. Although additional factors contribute to the epidemiology of colorectal cancer (43, 44), the significance of this antiproliferative pathway is highlighted by the neoplastic transformation of epithelial cells that follows loss of expression of endogenous GC-C ligands in the intestine (16-18). In turn, the conservation of GC-C itself and its downstream effectors by colorectal tumors provides a therapeutic target for restoration of this signaling cascade and maintenance of the tumor-suppressor phenotype. Indeed, oral administration of GC-C ligands or downstream effectors of that pathway, such as calcium, offer a hitherto unknown approach to the primary prevention of intestinal neoplasia and/or therapy of colorectal cancer metastases (29, 45-47).

References (Which are Each Incorporated Herein by Reference)

1 Ferlay, J., Bray, F., Pisani, P., & Parkin, D. M. (2001) in GLOBOCAN 2000: Cancer Incidence, Mortality and Prevalence Worldwide, Version 1.0 (International Agency for Research on Cancer, Lyon).
2. Hill, D. R. & Pearson, R. D. (1988). Ann. Intern. Med. 108, 839-852
3. Centers for Disease Control and Prevention. (2001) in Health Information for International Travel 1999-2000 (Department of Health and Human Services, Atlanta).
4. Schulz, S., Green, C. K., Yuen, P. S., & Garbers, D. L. (1990). Cell 63, 941-948
5. Hughes, J. M., Murad, F., Chang, B., & Guerrant, R. L. (1978). Nature 271, 755-756
6. Guarino, A., Cohen, M. B., & Giannella, R. A. (1987). Pediatr. Res. 21, 551-555
7. Giannella, R. A. (1995). J. Lab. Clin. Med. 125, 173-181
8. Carrithers, S. L., Barber, M. T., Biswas, S., Parkinson, S. J., Park, P. K., Goldstein, S. D., & Waldman, S. A. (1996). Proc. Natl. Acad. Sci. USA 93, 14827-14832
9. Parkinson, S. J., Alekseev, A. E., Gomez, L. A., Wagner, F., Terzic, A., & Waldman, S. A. (1997). J. Biol. Chem. 272, 754-758
10. Zhang, W., Mannan, I., Schulz, S., Parkinson, S. J., Alekseev, A. E., Gomez, L. A., Terzic, A., & Waldman, S. A. (1999). FASEB J. 13, 913-922
11. Vaandrager, A. B., Bot, A. G., Ruth, P., Pfeifer, A., Hofmann, F., & De Jonge, H. R. (2000). Gastroenterology 118, 108-114.
12. Currie, M. G., Fok, K. F., Kato, J., Moore, R. J., Hamra, F. K., Duffin, K. L., & Smith, C. E. (1992). Proc. Natl. Acad. Sci. USA 89, 947-951
13. Hamra, F. K., Forte, L. R., Eber, S. L., Pidhorodeckyj, N. V., Krause, W. J., Freeman, R. H., Chin, D. T., Tompkins, J. A., Fok, K. F., Smith, C. E., et al. (1993). Proc. Natl. Acad. Sci. USA 90, 10464-10468
14. Forte, L. R. (1999). Regul. Pept. 81, 25-39
15. Pitari, G. M., Di Guglielmo, M. D., Park, J., Schulz, S., & Waldman, S. A. (2001). Proc. Natl. Acad. Sci. USA 98, 7846-7851
16. Cohen, M. B., Hawkins, J. A., & Witte, D. P. (1998). Lab. Invest. 78, 101-108
17. Notterman, D. A., Alon, U., Sierk, A. J., & Levine, A. J. (2001). Cancer Res. 61, 3124-3130
18. Birkenkamp-Demtroder, K., Lotte Christensen, L., Harder Olesen, S., Frederiksen, C. M., Laiho, P., Aaltonen, L. A., Laurberg, S., Sorensen, F. B., Hagemann, R., & Orntoft, T. F. (2002). Cancer Res. 62, 4352-4363
19. Zingman, L. V., Alekseev, A. E., Bienengraeber, M., Hodgson, D., Karger, A. B., Dzeja, P. P., & Terzic, A. (2001). Neuron 31, 233-245
20. Vaandrager, A. B., Bot, A. G., & De Jonge, H. R. (1997). Gastroenterology 112, 437-443
21. Stern, J. H., Kaupp, U. B., & MacLeish, P. R. (1986). Proc. Natl. Acad. Sci. USA 83, 1163-1167
22. Dzeja, C., Hagen, V., Kaupp, U. B., & Frings, S. (1999). EMBO J. 18, 131-144
23. Devor, D. C. & Frizzell, R. A. (1998). Am. J. Physiol. 274, C138-C148
24. Hille, B. (1984) in Ionic Channels of Excitable Membranes (Sinauer Associates, Sunderland, Mass.).
25. Fukumoto, S., Koyama, H., Hosoi, M., Yamakawa, K., Tanaka, S., Morii, H., & Nishizawa, Y. (1999). Circ. Res. 85, 985-991
26. Fischer, T. A., Palmetshofer, A., Gambaryan, S., Butt, E., Jassoy, C., Walter, U., Sopper, S., & Lohmann, S. M. (2001). J. Biol. Chem. 276, 5967-5974
27. Sugimoto, T., Haneda, M., Togawa, M., Isono, M., Shikano, T., Araki, S., Nakagawa, T., Kashiwagi, A., Guan, K. L., & Kikkawa, R. (1996). J. Biol. Chem. 271, 544-547
28. Thompson, W. J., Piazza, G. A., Li, H., Liu, L., Fetter, J., Zhu, B., Sperl, G., Ahnen, D., & Pamukcu, R. (2000). Cancer Res. 60, 3338-3342
29. Shailubhai, K., Yu, H. H., Karunanandaa, K., Wang, J. Y., Eber, S. L., Wang, Y., Joo, N. S., Kim, H. D., Miedema, B. W., Abbas, S. Z., et al. (2000). Cancer Res. 60, 5151-5157
30. Hood, J. & Granger, H. J. (1998). J. Biol. Chem. 273, 23504-23508
31. Waldman, S. A., Barber, M., Pearlman, J., Park, J., George, R., & Parkinson, S. J. (1998). Cancer Epidemiol. Biomarkers Prev. 7, 505-514
32. Chao, A. C., de Sauvage, F. J., Dong, Y. J., Wagner, J. A., Goeddel, D. V., & Gardner, P. (1994). EMBO J. 13, 1065-1072
33. Ames, J. B., Dizhoor, A. M., Ikura, M., Palczewski, K., & Stryer, L. (1999). J. Biol. Chem. 274, 19329-19337
34. Zufall, F., Shepherd, G. M., & Barnstable, C. J. (1997). Curr. Opin. Neurobiol. 7, 404-412
35. Lucas, K. A., Pitari, G. M., Kazerounian, S., Ruiz Stewart, I., Park, J., Schulz, S., Chepenik, K. P., & Waldman, S. A. (2000). Pharmacol. Rev. 52, 375-414
36. Rosado, J. A., Porras, T., Conde, M., & Sage, S. O. (2001). J. Biol. Chem. 276, 15666-15675
37. Andric, S. A., Kostic, T. S., Tomic, M., Koshimizu, T., & Stojilkovic, S. S. (2001). J. Biol. Chem. 276, 844-849
38. Knoop, F. C. & Owens, M. (1992). J. Pharmacol. Toxicol. Methods 28, 67-72
39. Bhattacharya, J. & Chakrabarti, M. K. (1998). Biochim. Biophys. Acta 1403, 14
40. Qiu, W., Lee, B., Lancaster, M., Xu, W., Leung, S., & Guggino, S. E. (2000). Am. J. Physiol. 278, C336-C343
41. Biel, M., Sautter, A., Ludwig, A., Hofmann, F., & Zong, X. (1998). Naunyn-Schmiedeberg's Arch. Pharmacol. 358, 140-144
42. Berridge, M. J., Bootman, M. D., & Lisp, P. (1998). Nature 395, 645-648
43. Briskey, E. N. & Pamies, R. J. (2000). J. Natl. Med. Assoc. 92, 222-230
44. Wilmink, A. B. (1997). Dis. Colon Rectum 40, 483-493
45. Buset, M., Lipkin, M., Winawer, S., Swaroop, S., & Friedman, E. (1986). Cancer Res. 46, 5426-5430
46. Penman, I. D., Liang, Q. L., Bode, J., Eastwood, M. A., & Arends, M. J. (2000). J. Clin. Pathol. 53, 302-307
47. Sesink, A. L., Termont, D. S., Kleibeuker, J. H., & Van der Meer, R. (2001). Carcinogenesis 22, 1653-1659
48. Grider, J. R. (1993). Am. J. Physiol. 264, G334-G340
49. Butt, E., Eigenthaler, M., & Genieser, H. G. (1994). Eur. J. Pharmacol. 269, 265-268
50. Gadbois, D. M., Crissman, H. A., Tobey, R. A., & Bradbury, E. M. (1992). Proc. Natl. Acad. Sci. USA 89, 8626-8630
51. Dostmann, W. R. (1995). FEBS Lett. 375, 231-234
52. Harrison, S. A., Reifsnyder, D. H., Gallis, B., Cadd, G. G., & Beavo, J. A. (1986). Mol. Phar Example 4

The effect of GCC ligands on the component processes underlying metastasis cancer which has cells that expresses GCC has been studied. The metastatic process nominally involves three steps: digesting the underlying connective tissue, moving through the hole created by that digestion, and evading the trap of connective tissue underneath the hole that traps cells trying to escape from their normal compartment. Experiments used ST as the GCC ligand and colorectal cancer cells as the cancer which has cells that expresses GCC. Results indicate the following.

ST inhibited the release of matrix metalloproteinase 9, an enzyme that digests collagen upon which intestinal epithelial cells sit. Preventing the secretion of this digestive enzyme will inhibit the ability of these tumor cells to invade the wall of the intestine. A decrease in secretion was demonstrated by employing enzymology (MMP 9 activity) and protein analysis (western blot) in human colorectal cancer cells in vitro. ST did this at a concentration of 1 micromolar. The effects of ST are precisely mimicked by cylic GMP.

ST prevented human colorectal cancer cells from organizing their actin cytoskeleton. ST (1 micromolar) and cyclic GMP prevented this organization as observed by confocal microscopy, specifically staining actin filaments, and by cell spreading. The latter is a functional readout of the ability of cells to organize actin. Human colorectal cancer cells treated with ST cannot spread their bodies out in vitro. An inability to organize their actin cytoskeletons will prevent these cells from being able to migrate through tissues to metastasize.

ST selectively increased the affinity of human colorectal cancer cells for type IV collagen in vitro (ST at 1 micromolar). Type IV collagen forms the connective tissue meshwork supporting the lamina propria and specifically serves to trap cells through specific interactions with beta integrins. Cancer cells evade this trap by diminishing their ability to bind to type IV collagen. ST treatment increased by 2-fold, a significant change, the association of human colorectal cancer cells with type IV collagen, but not with laminin or fibronectin, making this a specific interaction. Enhancing this interaction will prevent metastases by trapping cells in the laminapropria underlying epithelial cells in the intestine. In addition to demonstrating selective increase of colorectal cancer cell affinity for type IV collagen, a component of the laminopropria, these data demonstrate the effects of ST on functions important to metastasis of gastric and esophageal cancer. Specifically the data demonstrate that ST inhibited the release of an enzyme involved in metastasis and prevented actin organization necessary for cell migration. These data support the conclusion that GCC ligands will inhibit metastasis of cancer cells that express GCC such as primary and metastatic colorectal, gastric and espophageal.

The invention claimed is:

1. A method of treating an individual who has metastasized colorectal cancer or primary or metastasized gastric or esophageal cancer in an individual who has been identified as having metastasized colorectal cancer or primary or metastasized gastric or esophageal cancer, said method comprising the steps in the following order:
   a) administering to said individual a cytostatically effective amount of a guanylyl cyclase C ligand sufficient to inhibit cell proliferation by the cytostatic effect of the guanylyl cyclase C ligand for at least 6 hours wherein, wherein said guanylyl cycles C ligand activates guanylyl cyclase C on cancer cells, and stimulates accumulation of intracellular cGMP, and
   b) subsequently after administration of said guanylyl cycles C ligand is completed administering a therapeutically effective amount of a cytotoxic therapeutic agent or radiation,
   wherein effectiveness of said therapeutically effective amount of a cytotoxic therapeutic agent or radiation is enhanced by prior inhibition of proliferation of cancer cells by said cytostatically effective amount of said guanylyl cyclase C ligand.

2. The method of claim 1 wherein said cytotoxic therapeutic agent is selected from the group consisting of: methotrexate, doxorubicin, daunorubicin, cytosinarabinoside, etoposide, 5- fluorouracil, melphalan, chlorambucil, cis-platin, vindesine, mitomycin, bleomycin, purothionin, macromomycin, 1,4 benzoquinone derivatives, trenimon, ricin, ricin A chain, *Pseudomonas* exotoxin, diphtheria toxin, *Clostridium perfringens* phospholipase C, bovine pancreatic ribonuclease, pokeweed antiviral protein, abrin, abrin A chain, cobra venom factor, gelonin, saporin, modeccin, viscumin, volkensin, nitroimidazole, metronidazole and misonidazole.

3. The method of claim 1 wherein the individual has been identified as having metastatic colorectal, esophageal or stomach cancer.

4. The method of claim 1, wherein the cytostatically effective amount of a guanylyl cyclase C ligand is an amount sufficient to maintain a concentration of greater than or equal to 10 times the $EC_{50}$ of said guanylyl cyclase C ligand.

5. The method of claim 1 wherein said cytotoxic therapeutic agent is a guanylyl cyclase C ligand conjugated to a cytotoxic moiety.

6. The method of claim 5 wherein said cytotoxic therapeutic agent is an anti-guanylyl cyclase C antibody conjugated to a cytotoxic moiety.

7. The method of claim 1 wherein the guanylyl cyclase C ligand that activates guanylyl cyclase C on cancer cells is administered in an amount sufficient to inhibit cell proliferation by the cytostatic effect of the guanylyl cyclase C ligand for at least 8 hours.

8. The method of claim 1 wherein the guanylyl cyclase C ligand that activates guanylyl cyclase C on cancer cells is administered in an amount sufficient to inhibit cell proliferation by the cytostatic effect of the guanylyl cyclase C ligand for at least 12 hours.

9. The method of claim 1 wherein the guanylyl cyclase C ligand that activates guanylyl cyclase C on cancer cells is administered in an amount sufficient to inhibit cell proliferation by the cytostatic effect of the guanylyl cyclase C ligand for at least 16 hours.

10. The method of claim 1 wherein the guanylyl cyclase C ligand that activates guanylyl cyclase C on cancer cells is administered in an amount sufficient to inhibit cell proliferation by the cytostatic effect of the guanylyl cyclase C ligand for at least 20 hours.

11. The method of claim 1 wherein the guanylyl cyclase C ligand that activates guanylyl cyclase C on cancer cells is administered in an amount sufficient to inhibit cell proliferation by the cytostatic effect of the guanylyl cyclase C ligand for at least 24 hours.

12. The method of claim 1 wherein said guanylyl cyclase C ligand that activates guanylyl cyclase C on cancer cells is administered intravenously.

13. The method of claim 1 wherein said guanylyl cyclase C ligand that activates guanylyl cyclase C is administered for 7-15 days followed by treatment using said cytotoxic agent.

14. The method of claim 1 wherein said guanylyl cyclase C ligand that activates guanylyl cyclase C is administered for 30 days followed by treatment using said cytotoxic agent.

15. The method of claim 1 comprising administering more than one cytotoxic agent.

16. The method of claim 1 comprising administering one cytotoxic agent that selectively kills cells in S phase and one cytotoxic drug that selectively kills cells in G1 phase.

17. The method of claim 1 wherein said cytotoxic therapeutic agent is selected from the group consisting of: methotrexate, doxorubicin, daunorubicin, cytosinarabinoside, etoposide, 5- fluorouracil, melphalan, chlorambucil, cis-platin, vindesine, mitomycin, bleomycin, purothionin, macromomycin, 1,4 benzoquinone derivatives, nitroimidazole, metronidazole and misonidazole.

18. A method of treating an individual who has metastasized colorectal cancer or primary or metastasized gastric or esophageal cancer in an individual who has been identified as having metastasized colorectal cancer or primary or metastasized gastric or esophageal cancer, said method comprising the steps in the following order:
a) administering to said individual for a period sufficient to inhibit the proliferation of cancer cells, a cytostatically effective amount of a guanylyl cyclase C ligand that activate guanylyl cyclase C on cancer cells, wherein said activation of guanylyl cyclase C stimulates intracellular accumulation of cGMP and inhibits proliferation of said cancer cells; and
b) subsequently after administration of said guanylyl cyclase C ligand is completed administering a therapeutically effective amount of a cytotoxic therapeutic agent or radiation;
wherein effectiveness of said therapeutically effective amount of a cytotoxic therapeutic agent or radiation is enhanced by prior inhibition of proliferation of cancer cells by said cytostatically effective amount of said guanylyl cyclase C ligand.

19. The method of claim 18 wherein said cytotoxic therapeutic agent is selected from the group consisting of: methotrexate, doxorubicin, daunorubicin, cytosinarabinoside, etoposide, 5- fluorouracil, melphalan, chlorambucil, cis-platin, vindesine, mitomycin, bleomycin, purothionin, macromomycin, 1,4 benzoquinone derivatives, trenimon, ricin, ricin A chain, *Pseudomonas* exotoxin, diphtheria toxin, *Clostridium perfringens* phospholipase C, bovine pancreatic ribonuclease, pokeweed antiviral protein, abrin, abrin A chain, cobra venom factor, gelonin, saporin, modeccin, viscumin, volkensin, nitroimidazole, metronidazole and misonidazole.

20. The method of claim 18 wherein the individual has been identified as having metastatic colorectal, esophageal or stomach cancer.

21. The method of claim 18 wherein said cytotoxic therapeutic agent is a guanylyl cyclase C ligand conjugated to a cytotoxic moiety.

22. The method of claim 18 wherein said cytotoxic therapeutic agent is an anti-guanylyl cyclase C antibody conjugated to a cytotoxic moiety.

23. The method of claim 18 wherein said guanylyl cyclase C ligand that activates guanylyl cyclase C on cancer cells is administered intravenously.

24. The method of claim 18 comprising administering more than one cytotoxic agent.

25. The method of claim 18 comprising administering one cytotoxic agent that selectively kills cells in S phase and one cytotoxic drug that selectively kills cells in G1 phase.

26. The method of claim 18 wherein said cytotoxic therapeutic agent is selected from the group consisting of: methotrexate, doxorubicin, daunorubicin, cytosinarabinoside, etoposide, 5- fluorouracil, melphalan, chlorambucil, cis-platin, vindesine, mitomycin, bleomycin, purothionin, macromomycin, 1,4 benzoquinone derivatives, nitroimidazole, metronidazole and misonidazole.

* * * * *